US008642008B2

(12) United States Patent
Inagaki et al.

(10) Patent No.: US 8,642,008 B2
(45) Date of Patent: Feb. 4, 2014

(54) MOLECULAR PROBE FOR IMAGING OF PANCREATIC ISLETS AND USE OF THE SAME

(75) Inventors: Nobuya Inagaki, Kyoto (JP); Hideo Saji, Kyoto (JP); Kentaro Toyoda, Kyoto (JP); Hiroyuki Kimura, Kyoto (JP); Yu Ogawa, Kyoto (JP); Konomu Hirao, Kyoto (JP); Kenji Nagakawa, Kyoto (JP); Hirokazu Matsuda, Kyoto (JP)

(73) Assignees: Kyoto University, Kyoto (JP); ARKRAY, Inc., Kyoto (JP)

( * ) Notice: Subject to any disclaimer, the term of this patent is extended or adjusted under 35 U.S.C. 154(b) by 212 days.

(21) Appl. No.: 12/872,837

(22) Filed: Aug. 31, 2010

(65) Prior Publication Data

US 2011/0059483 A1 Mar. 10, 2011

Related U.S. Application Data

(60) Provisional application No. 61/272,282, filed on Sep. 8, 2009.

(30) Foreign Application Priority Data

Sep. 4, 2009 (JP) .................................. 2009-204769
Mar. 16, 2010 (WO) .................. PCT/JP2010/054450

(51) Int. Cl.
*A61K 51/08* (2006.01)
(52) U.S. Cl.
USPC .......... 424/1.85; 424/1.69; 530/303; 530/326
(58) Field of Classification Search
None
See application file for complete search history.

(56) References Cited

U.S. PATENT DOCUMENTS

| 5,624,659 A * | 4/1997 | Bigner et al. ................ 424/1.49 |
| 2009/0180953 A1 | 7/2009 | Gotthardt et al. ............ 424/1.69 |
| 2012/0087863 A1 * | 4/2012 | Saji et al. ....................... 424/9.1 |
| 2013/0052132 A1 * | 2/2013 | Saji et al. ..................... 424/1.69 |

FOREIGN PATENT DOCUMENTS

| EP | 1867634 | 12/2007 |
| JP | 09-292466 | 11/1997 |
| WO | WO 2004/035744 | 4/2004 |
| WO | WO 2006/107106 | 10/2006 |
| WO | 2008/072973 A2 | 6/2008 |

OTHER PUBLICATIONS

Wang, Z. et al; "Glucagon like peptide 1 is a physiological incretin in rat." J. Clin. Invest. (1995) 95 p. 417-421.*
Goke R. et al; "Extendin-4 is a high potency agonist and truncated extendin (9-39)amide an antagonist at the glucagon like peptide 1-(7-36) amide receptor of insulin secreting beta cells." J. Bio. Chem. (1993) 268(26) p. 19650-19655.*
Goke, Rudiger et al; "Exendin-4 is a high potency agonist and truncated exendin(9-39) amide an antagonist at the glucagon like peptide 1 (7-36) amide receptor of insulin secreting beta cells." J. Bio. Chem (1993) 268 (26) p. 19650-19655.*
Vaidyanathan, Ganesan and Zalutsky, Michael R. "Protein radiohalogenation: Observations on the design ofn-succinimidyl ester acylation agents." Bioconjugate Chem. (1990) 1 p. 269-273.*
Matsumoto, Ken-Ichi et al; "The distribution of tenascin-X is distinct and often rfeciprocal to that of tenascin-C." J. Cell. Bio.; (1994) 125(2) p. 483-493.*
Perkin Elmer web page of iodinated compounds, http://www.perkinelmer.com/Catalog/Category/ID/Iodinated%20Compounds%20AL.*
Runge, Steffen et al; "Differential structural properties of glp-1 and exendin-4 determine their relative affinity for the glp-1 receptor n-terminal extracellular domain." Biochemistry (2007) 46(19) p. 5830-5840.*
Vaidyanathan, Ganessan and Zalutsky, Michael R.; "Protein radiohalogenation: observations on the design of n-succinimidyl ester acylation agents." Bioconjugate chem. (1990) 1 p. 269-273.*

(Continued)

*Primary Examiner* — Cecilia J Tsang
*Assistant Examiner* — Fred Reynolds
(74) *Attorney, Agent, or Firm* — Morgan, Lewis & Bockius LLP

(57) ABSTRACT

To provide a molecular probe for imaging of pancreatic islets. A molecular probe for use in imaging of pancreatic islets is provided. The molecular probe includes any one of the following polypeptides: polypeptides represented by the following formulae (1), (5), and (9); and polypeptides having homology with the foregoing polypeptides:

| Z-DLSXQMEEEAVRLFIEWLKNGGPSSGAPPPS-NH$_2$ | (1) |
| Z-DLSKQMEEEAVRLFIEWLXNGGPSSGAPPPS-NH$_2$ | (5) |
| B-DLSKQMEEEAVRLFIEWLKNGGPSSGAPPPS-NH$_2$ | (9) | where X in the formulae (1) and (5) and B- in the formula (9) indicate that an amino group is labeled with a group represented by the formula (I) below having an aromatic ring,

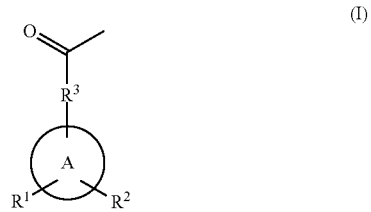

(I)

wherein A represents either an aromatic hydrocarbon group or an aromatic heterocyclic group, $R^1$ represents a substituent that contains radioactive iodine, $R^2$ represents either a hydrogen atom or a substituent different from that represented by $R^1$, and $R^3$ represents any one of a bond, a methylene group, and an oxymethylene group.

9 Claims, 7 Drawing Sheets

(56) References Cited

OTHER PUBLICATIONS

Arkray, Inc., "Leading research on molecular imaging device for supporting treatment of malignant tumor, etc. / development of method for ultra-early diagnosis of diabetes by noninvasive in-vivo pancreatic islets imaging", Interim report of Heisei 19 (2007) fiscal year, out of Heisei 19 to 20 (2007 to 2008) years (Sep. 19, 2008) (partial (pp. 1,5) translation provided).
S. Al-Sabah et al., "The positive charge at Lys-288 of the glucagon-like peptide-1 (GLP-1) receptor is important for binding the N-terminus of peptide agonists", FEBS Letters 553: 342-346 (2003).
M. Behe et al., "Are radiolabeled GLP-1 receptor antagonists useful for scintigraphy?", 2009 SNM Annual Meeting, abstract, Oral Presentations No. 327 (May 2009).
M. Brom et al., "$^{68}$Ga-labelled exendin-3, a new agent for the detection of insulinomas with PET", Eur. J. Nucl. Med. Mol. Imaging 37: 1345-1355 (2010).
E. Christ et al., "Glucagon-Like Peptide-1 Receptor Imaging for Localization of Insulinomas", J. Clin. Endocrinol Metab. 94(11): 4398-4405 (Nov. 2009).
R. Göke et al., "Exendin-4 is a High Potency Agonist and Truncated Exendin-(9-39)-amide an Antagonist at the Glucagon-like Peptide 1-(7-36)-amide Receptor of Insulin-secreting β-Cells", J. Biol. Chem. 268(26): 19650-19655 (1993).
M. Gotthardt et al., "Use of the incretin hormone glucagon-like peptide-1 (GLP-1) for the detection of insulinomas: initial experimental results", European Journal of Nuclear Medicine 29(5): 598-606 (May 2002).
M. Gotthardt et al., "A new technique for in vivo imaging of specific GLP-1 binding sites: First results in small rodents", Regulatory Peptides 137: 162-167 (2006).
B.D. Green et al., "Chronic treatment with exendin(9-39)amide indicates a minor role for endogenous glucagon-like peptide-1 in metabolic abnormalities of obesity-related diabetes in ob/ob mice", J. Endocrinol. 185: 307-317 (2005).
K. Hirao "Leading research on molecular imaging device for supporting treatment of malignant tumor, etc. / Development of method for ultra-early diagnosis of diabetes by noninvasive in-vivo pancreatic islet imaging", Interim report of Heisei 20 (2008) Fiscal Year, out of Heisei 19 to 20 (2007-2008) years (May 20, 2009) (partial (pp. 1,2) translation provided).
N. Inagaki, "Research on development of method for ultra-early diagnosis of diabetes by noninvasive in-vivo pancreatic islet imaging", Heisei 19 (2007) Fiscal Year Overview Research Report, Research Project for Medical Equipment Development Promotion, Grants-in-Aid for Scientific Research from Ministry of Health, Labor and Welfare (Apr. 20, 2008) (partial (pp. 1-7, 10-15, 24, 25) translation provided).
N. Inagaki, "Research on development of method for ultra-early diagnosis of diabetes by noninvasive in-vivo pancreatic islet imaging", Heisei 20 (2008) Fiscal Year Overview Research Report, Research Project for Medical Equipment Development Promotion, Grants-in-Aid for Scientific Research from Ministry of Health, Labor and Welfare (Apr. 21, 2009) (partial (pp. 1-7, 10-17, 23, 24) translation provided).
N. Inagaki, "Development of method for ultra-early diagnosis of diabetes by noninvasive in-vivo pancreatic islet imaging", Research of New Medical Devices 13, 72-73 (Mar. 25, 2008) (partial (pp. 72, 73) translation provided).
H. Kimura et al., "Development of in vivo imaging agents targeting glucagon-like peptide-1 receptor (GLP-1R) in pancreatic islets", 2009 SNM Annual Meeting, abstract, Oral Presentations No. 326 (May 2009).
E. Mukai et al., "Non-invasive imaging of pancreatic islets targeting glucagon-like peptide-1-receptors", 44th EASD Annual Meeting (Rome), abstract, Presentation No. 359 (2008).
E. Mukai et al., "GLP-1 receptor antagonist as a potential probe for pancreatic B-cell imaging", Biophys. Res. Commun. 389(3): 523-526 (2009).
J. W. Neidigh et al., "Exendin-4 and Glucagon-like peptide-1: NMR Structural Comparisons in the Solution and Micelle-Associated States", Biochemistry 40: 13188-13200 (2001).
U. Ritzel et al., "A synthetic glucagon-like peptide-1 analog with improved plasma stability", Journal of Endocrinology 159: 93-102 (1998).
J. Schirra et al., "Exendin(9-39)amide Is an Antagonist of Glucagon-like Peptide-1)7-36)amide in Humans", J. Clin. Invest. 101(7): 1421-1430 (Apr. 1998).
G. Vaidyanathan et al., "Protein Radiohalogenation: Observations on the Design of N-Succinimidyl Ester Acylation Agents", Bioconjug. Chem. 1(4), 269-273 (Jul. 1990).
G. Vaidyanathan et al., "Radioiodination of Proteins Using N-Succinimidyl 4-Hydroxy-3-iodobenzoate", Bioconjug. Chem. 4(1), 78-84 (Jan. 1993).
A. Wicki et al., "[Lys$^{40}$(Ahx-DTPA-$^{111}$In)NH$_2$]-Exendin-4 is a Highly Efficient Radiotherapeutic for Glucagon-Like Peptide-1 Receptor-Targeted Therapy for Insulinoma", Clin. Cancer Res. 13(12): 3696-3705 (Jun. 15, 2007).
D. Wild et al., "[Lys$^{40}$(Ahx-DTPA-$^{111}$In)NH$_2$]Exendin-4, a Very Promising Ligand for Glucagon-like Peptide-1 (GLP-1) Receptor Targeting", J. Nucl. Med. 47: 2025-2033 (2006).

\* cited by examiner

US 8,642,008 B2

MOLECULAR PROBE FOR IMAGING OF PANCREATIC ISLETS AND USE OF THE SAME

TECHNICAL FIELD

The present invention relates to a molecular probe for imaging of pancreatic islets, and relates to use of the same.

BACKGROUND ART

Today, type-II diabetics are continuously increasing in Japan, and the estimated number of the same exceeds 8,200,000. As a measure against this increase, interventions for preventing diabetes from developing have been made based on the glucose tolerance test, resulting, however, in unsatisfactory effects. The cause is as follows: at such a borderline stage that functional abnormalities are found by the glucose tolerance test, disorders of pancreatic islets have already advanced to a high degree, and this stage possibly is too late as a time for starting interventions.

More specifically, in the diabetes developing process, the amount of pancreatic islets (particularly, the amount of pancreatic β-cells) decreases prior to the occurrence of glucose tolerance abnormalities. Therefore, when functional abnormalities are detected or there are subjective symptoms, diabetes has already reached the stage where it is too difficult to be treated. On the other hand, if a decrease in the amount of pancreatic islets and/or the amount of pancreatic β-cells can be detected at an early stage, there is a possibility for the prevention and treatment of diabetes. Therefore, a noninvasive technique for imaging pancreatic islets, particularly a noninvasive technique for imaging pancreatic islets for determining the amount of the pancreatic islets and/or the amount of pancreatic β-cells, has been desired for the prevention and diagnosis of diabetes. Among the noninvasive techniques, a molecular probe that enables imaging of pancreatic islets, preferably pancreatic β-cell, and noninvasive determination of an amount of pancreatic β-cells has been desired in particular.

In designing a molecular probe for imaging of pancreatic islets, various target molecules in pancreatic islet cells, particularly functional proteins specific for the β-cells, are being researched. Among these molecular probes, GLP-1R (glucagon-like peptide-1 receptor) is being researched as a target molecule; GLP-1R is distributed in pancreatic β-cells, and is a seven-transmembrane G protein coupled receptor.

As a molecular probe for pancreatic β-cells imaging that uses GLP-1R as a target molecule, a molecular probe obtained by labeling a derivative of exendin-4(9-39) as a GLP-1R antagonist with [$^{18}$F] fluorine has been researched (e.g., H. Kimura et al. Development of in vivo imaging agents targeting glucagons-like peptide-1 receptor (GLP-1R) in pancreatic islets. 2009 SNM Annual Meeting, abstract, Oral Presentations No. 326 (Document 1)).

Further, a molecular probe for imaging a GLP-1R-positive tumor has been researched as an imaging probe targeting GLP-1R as a target molecule. Examples of the molecular probe for imaging a GLP-1R-positive tumor include a molecular probe obtained by labeling a derivative of exendin-4 as an GLP-1R agonist with [min] indium via diethylenetriaminepentaacetic acid (DTPA); and a molecular probe obtained by labeling a derivative of exendin-4(9-39) as a GLP-1R antagonist with [$^{111}$-In] indium via DTPA (e.g., M. Beche et al. Are radiolabeled GLP-1 receptor antagonists useful for scintigraphy? 2009 SNM Annual Meeting, abstract, Oral Presentations No. 327 (Document 2)).

However, another molecular probe for imaging of pancreatic islets is ultimately preferred to enable noninvasive three-dimensional imaging of pancreatic islets.

DISCLOSURE OF INVENTION

The present invention provides a molecular probe for imaging of pancreatic islets that enables noninvasive three-dimensional imaging of the pancreatic islets.

The present invention relates to a molecular probe for use in imaging of pancreatic islets, the molecular probe comprising any one of the following polypeptides:

a polypeptide represented by any one of the following formulae (1) to (12);

a polypeptide obtained by deletion, insertion, or substitution of one to several amino acids with respect to a polypeptide represented by any one of the following formulae (1) to (12), the polypeptide being capable of binding to pancreatic islets; and a polypeptide having a homology of 80% or higher with any one of the amino acid sequences of polypeptides represented by the following formulae (1) to (12), the polypeptide being capable of binding to pancreatic islets,

```
                                              (SEQ ID NO. 1)
Z-DLSXQMEEEAVRLFIEWLKNGGPSSGAPPPS-NH₂      (1)

(SEQ ID NO. 2)
Z-LSXQMEEEAVRLYIEWLKNGGPSSGAPPPS-NH₂       (2)

(SEQ ID NO. 3)
Z-SXQMEEEAVRLFIEWLKNGGPSSGAPPPS-NH₂        (3)

(SEQ ID NO. 4)
Z-XQMEEEAVRLFIEWLKNGGPSSGAPPPS-NH₂         (4)

(SEQ ID NO. 5)
Z-DLSKQMEEEAVRLFIEWLXNGGPSSGAPPPS-NH₂      (5)

(SEQ ID NO. 6)
Z-LSKQMEEEAVRLFIEWLXNGGPSSGAPPPS-NH₂       (6)

(SEQ ID NO. 7)
Z-SKQMEEEAVRLFIEWLXNGGPSSGAPPPS-NH₂        (7)

(SEQ ID NO. 8)
Z-KQMEEEAVRLFIEWLXNGGPSSGAPPPS-NH₂         (8)

(SEQ ID NO. 9)
B-DLSKQMEEEAVRLFIEWLKNGGPSSGAPPPS-NH₂      (9)

(SEQ ID NO. 10)
B-LSKQMEEEAVRLFIEWLKNGGPSSGAPPPS-NH₂       (10)

(SEQ ID NO. 11)
B-SKQMEEEAVRLFIEWLKNGGPSSGAPPPS-NH₂        (11)

(SEQ ID NO. 12)
B-KQMEEEAVRLFIEWLKNGGPSSGAPPPS-NH₂         (12)
``` where, in the foregoing formulae (1) to (8),

Z- indicates that an α-amino group at an N-terminus is either not modified, or is modified with a modifying group having no electric charge, and X represents a lysine residue, an amino group of a side chain of the lysine residue being labeled with a group represented by the following formula (I) having an aromatic ring, and in the formulae (9) to (12), B- indicates that an α-amino group at an N-terminus is labeled with a group represented by the following chemical formula (I) having an aromatic ring, and in the foregoing formulae (1) to (12), —NH$_2$ indicates that a carboxyl group at a C-terminus is amidated,

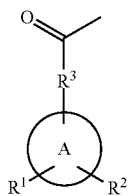

(I)

wherein

A represents either an aromatic hydrocarbon group or an aromatic heterocyclic group, R$^1$ represents a substituent that contains any one of $^{123}$I, $^{124}$I, $^{125}$I, and $^{131}$I, R$^2$ represents either a hydrogen atom, or one or more substituents different from that represented by R$^1$, and R$^3$ represents any one of a bond, a methylene group, and an oxymethylene group.

The present invention enables imaging of pancreatic islets, preferably three-dimensional imaging of pancreatic islets, and more preferably noninvasive imaging of pancreatic islets by, for example, positron emission tomography (PET) or single photon emission computed tomography (SPECT).

DESCRIPTION OF THE INVENTION

Figure 1A:
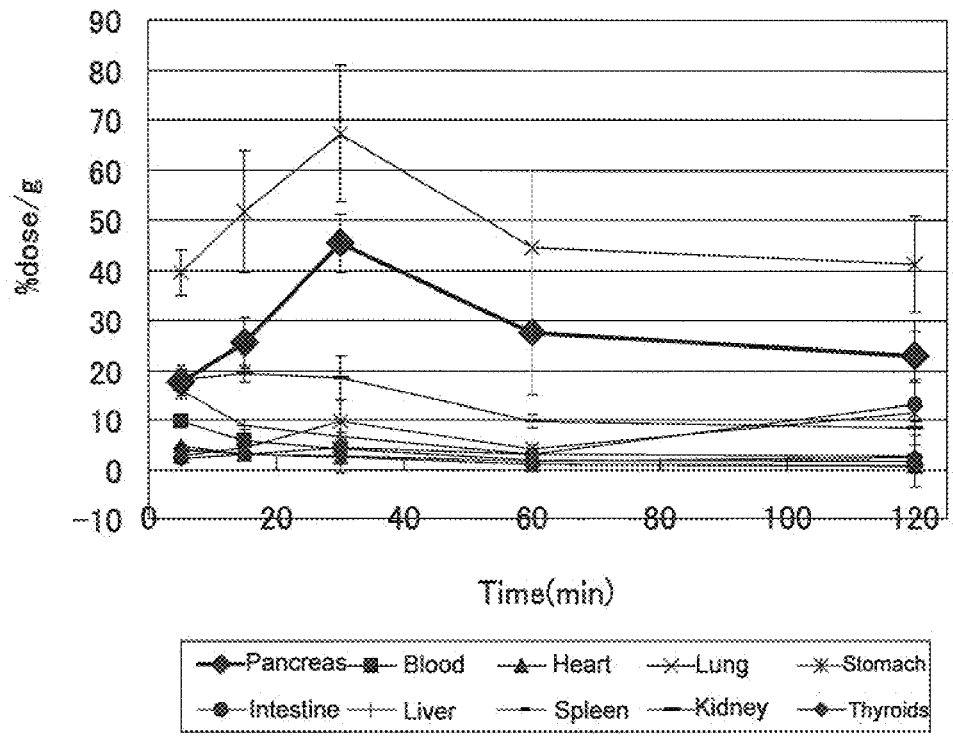
FIGS. 1A and 1B show exemplary graphs showing variations with time of biodistribution of a molecular probe for imaging of pancreatic islets according to Example 1.

The diameter of a pancreatic islet is, for example, approximately 50 to 500 μm in the case of a human. In order to noninvasively image or quantify such pancreatic islets in vivo, a molecular probe, for example, is considered to be necessary to show specific uptake in pancreatic islets, thereby making contrast between pancreatic islets and surrounding organs. Various researches and developments of molecular probes therefore have been made.

For example, Document 2 (M. Beche et al.) reports the research on the affinity of Lys$^{40}$(Ahx-DTPA-$^{111}$In)Exendin-(9-39) with respect to GLP-1R in GLP-1R-positive tumors and pancreatic islet cells. According to this document, the following was proven consequently: the uptake of Lys$^{40}$(Ahx-DTPA-$^{111}$In)Exendin-(9-39) in pancreatic islets was about 0.4%, and the uptake thereof in the GLP-1R-positive tumor cells was about 7.5%. In other words, the results show that Lys$^{40}$(Ahx-DTPA-$^{111}$In)Exendin-(9-39) has a low affinity with respect to GLP-1R.

In addition to these, the detection of pancreatic β-cells by targeting GLP-1R as a target molecule is attempted with use of a commercially available [$^{125}$I] Bolton-Hunter-labeled Extendin (9-39) (Perkin Elmer Inc.) (E. Mukai et al. Noninvasive imaging of pancreatic islets targeting glucagon-like peptide-1 receptors, 44$^{th}$ EASD Annual Meeting Rome 2008, abstract, Presentation No. 359 (Document 3). The following results have been obtained: when [$^{125}$I] Bolton-Hunter-labeled Exendin (9-39) (hereinafter referred to also as "BH-labeled probe") was administered to mice via tail veins thereof, the uptake of the BH-labeled probe in the pancreas was highest among those in the other organs except for the lungs during a time period from the point of 60 minutes to the point of 120 minutes after the administration. On the other hand, according to the results of experiments by the inventors of the present invention, after [$^{125}$I] Bolton-Hunter-labeled Exendin (9-39) was administered, uptake of the BH-labeled probe in the neck (the thyroid grand) increased with time (see, for example, FIGS. 2A and 2B of the present application). The increase of uptake in the neck (the thyroid grand) means that radioactive iodine was eliminated in vivo from the BH-labeled probe administered, and the radioactive iodine thus eliminated accumulated in the thyroid gland. It is known that the radioactive iodine, such as $^{125}$I, is easily accumulated in the thyroid gland, and once it is accumulated in the thyroid gland, it causes a thyroid gland cancer, etc. Therefore, a molecular probe with radioactive iodine as a radioactive nuclide preferably exhibits small accumulation of eliminated radioactive iodine in the neck (the thyroid gland); that is, a molecular probe that exhibits small elimination of radioactive iodine in vivo, thereby having excellent biological stability, is preferred.

Therefore, currently, a new molecular probe is sought for accumulating specifically in pancreatic islets, thereby generating contrast with surrounding organs, and for eliminating radioactive iodine from the molecular probe in vivo is suppressed.

The present invention is based on the finding that the molecular probe for imaging of pancreatic islets, labeled with the group represented by the chemical formula (I) above enables noninvasive three-dimensional imaging of pancreatic islets by, for example, PET, or SPECT, and that the elimination of radioactive iodine from the probe is suppressed. In other words, the present invention preferably achieves an effect of enabling noninvasive three-dimensional imaging of pancreatic islets. Further, since the molecular probe of the present invention preferably can accumulate more specifically in pancreatic islets, as compared with the molecular probes disclosed by Documents 1, 2, and 3, the present invention can achieve an effect of enabling the imaging of pancreatic islets for quantification.

Further, as described above, it is known that in the diabetes developing process, the amount of pancreatic islets decreases prior to the occurrence of glucose tolerance abnormalities. Therefore, by performing imaging of pancreatic islets and/or determining the amount of pancreatic islets, for example, minute changes in pancreatic islets can be found in a state prior to the development of diabetes or in an initial stage of the same, whereby the ultra-early detection and diagnosis of diabetes are enabled by the molecular probe for imaging of pancreatic islets of the present invention. Thus, the molecular probe for imaging of pancreatic islets of the present invention is useful for the prevention, early detection, and diagnosis of diabetes, preferably for the ultra-early detection and diagnosis of diabetes.

More specifically, the present invention relates to the following:

[1] A molecular probe for use in imaging of pancreatic islets, the molecular probe comprising any one of the following polypeptides:

a polypeptide represented by any one of the following formulae (1) to (12);

a polypeptide obtained by deletion, insertion, or substitution of one to several amino acids with respect to a polypeptide represented by any one of the following formulae (1) to (12), the polypeptide being capable of binding to pancreatic islets; and a polypeptide having a homology of 80% or higher with any one of the amino acid sequences of polypeptides represented by the following formulae (1) to (12), the polypeptide being capable of binding to pancreatic islets:

```
                                              (SEQ ID NO. 1)
Z-DLSXQMEEEAVRLFIEWLKNGGPSSGAPPPS-NH₂    (1)

(SEQ ID NO. 2)
Z-LSXQMEEEAVRLFIEWLKNGGPSSGAPPPS-NH₂     (2)

(SEQ ID NO. 3)
Z-SXQMEEEAVRLFIEWLKNGGPSSGAPPPS-NH₂      (3)

(SEQ ID NO. 4)
Z-XQMEEEAVRLFIEWLKNGGPSSGAPPPS-NH₂       (4)

(SEQ ID NO. 5)
Z-DLSKQMEEEAVRLFIEWLXNGGPSSGAPPPS-NH₂    (5)

(SEQ ID NO. 6)
Z-LSKQMEEEAVRLFIEWLXNGGPSSGAPPPS-NH₂     (6)

(SEQ ID NO. 7)
Z-SKQMEEEAVRLFIEWLXNGGPSSGAPPPS-NH₂      (7)

(SEQ ID NO. 8)
Z-KQMEEEAVRLFIEWLXNGGPSSGAPPPS-NH₂       (8)

(SEQ ID NO. 9)
B-DLSKQMEEEAVRLFIEWLKNGGPSSGAPPPS-NH₂    (9)

(SEQ ID NO. 10)
B-LSKQMEEEAVRLFIEWLKNGGPSSGAPPPS-NH₂     (10)

(SEQ ID NO. 11)
B-SKQMEEEAVRLFIEWLKNGGPSSGAPPPS-NH₂      (11)

(SEQ ID NO. 12)
B-KQMEEEAVRLFIEWLKNGGPSSGAPPPS-NH₂       (12)
``` where in the foregoing formulae (1) to (8),

Z- indicates that an α-amino group at an N-terminus is either not modified, or is modified with a modifying group having no electric charge, and X represents a lysine residue, an amino group of a side chain of the lysine residue being labeled with a group represented by the chemical formula (I) below having an aromatic ring, in the formulae (9) to (12), B- indicates that an α-amino group at an N-terminus is labeled with a group represented by the chemical formula (I) below having an aromatic ring, and in the foregoing formulae (1) to (12), —NH₂ indicates that a carboxyl group at a C-terminus is amidated,

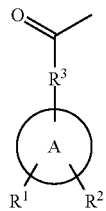

(I)

A represents either an aromatic hydrocarbon group or an aromatic heterocyclic group, $R^1$ represents a substituent that contains any one of $^{123}I$, $^{124}I$, $^{125}I$, and $^{131}I$, $R^2$ represents either a hydrogen atom, or one or more substituents different from that represented by $R^1$, and $R^3$ represents any one of a bond, a methylene group, and an oxymethylene group;

[2] The molecular probe for imaging of pancreatic islets according to [1], wherein the group having an aromatic ring is a group represented by the following chemical formula (II):

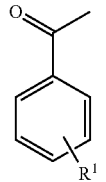

(II)

wherein $R^1$ represents a substituent that contains any one of $^{123}I$, $^{124}I$, $^{125}I$, and $^{131}I$;

[3] A kit for performing imaging of pancreatic islets, comprising the molecular probe for imaging of pancreatic islets according to [1] or [2];

[4] The kit according to [3], wherein the molecular probe for imaging of pancreatic islets included in the kit is in a form of a parenteral solution;

[5] A reagent for performing imaging of pancreatic islets, comprising the molecular probe for imaging of pancreatic islets according to [1] or [2];

[6] A method for imaging of pancreatic islets comprising detecting a signal of the molecular probe for imaging of pancreatic islets according to [1] or [2] from an analyte to which the molecular probe has been administered;

[7] The method for imaging of pancreatic islets according to [6], further comprising determining a state of pancreatic islets from results of the imaging of pancreatic islets using the molecular probe for imaging of pancreatic islets;

[8] A method for determining an amount of pancreatic islets, comprising;

detecting a signal of the molecular probe for imaging of pancreatic islets according to [1] or [2] from an analyte to which the molecular probe has been administered; and calculating an amount of pancreatic islets from the detected signal of the molecular probe for imaging of pancreatic islets;

[9] The method for determining an amount of pancreatic islets according to [8], further comprising presenting the calculated amount of pancreatic islets;

[10] A method for producing the molecular probe for imaging of pancreatic islets according to [1] or [2], comprising labeling and deprotecting a precursor of the molecular probe for imaging of pancreatic islets, wherein the precursor of the molecular probe for imaging of pancreatic islets includes any one of the following polypeptides:

a polypeptide represented by any one of the following formulae (13) to (24);

a polypeptide obtained by deletion, insertion, or substitution of one to several amino acids with respect to a polypeptide represented by any one of the following formulae (13) to (24), the polypeptide being capable of binding to pancreatic islets after being labeled and deprotected; and a polypeptide having a homology of 80% or higher with any one of the amino acid sequences of polypeptides represented by the following formulae (13) to (24), the polypeptide being capable of binding to pancreatic islets after being labeled and deprotected,

```
                                          (SEQ ID NO. 13)
*-DLSKQMEEEAVRLFIEWLK* NGGPSSGAPPPS-NH₂        (13)

(SEQ ID NO. 14)
 *-LSKQMEEEAVRLFIEWLK* NGGPSSGAPPPS-NH₂        (14)

(SEQ ID NO. 15)
  *-SKQMEEEAVRLFIEWLK* NGGPSSGAPPPS-NH₂        (15)

(SEQ ID NO. 16)
   *-KQMEEEAVRLFIEWLK* NGGPSSGAPPPS-NH₂        (16)

(SEQ ID NO. 17)
*-DESK* QMEEEAVRLFIEWLKNGGPSSGAPPPS-NH₂        (17)

(SEQ ID NO. 18)
 *-LSK* QMEEEAVRLFIEWLKNGGPSSGAPPPS-NH₂        (18)

(SEQ ID NO. 19)
  *-SK* QMEEEAVRLFIEWLKNGGPSSGAPPPS-NH₂        (19)

(SEQ ID NO. 20)
   *-K* QMEEEAVRLFIEWLKNGGPSSGAPPPS-NH₂        (20)

(SEQ ID NO. 21)
DLSK* QMEEEAVRLFIEWLK* NGGPSSGAPPPS-NH₂        (21)

(SEQ ID NO. 22)
 LSK* QMEEEAVRLFIEWLK* NGGPSSGAPPPS-NH₂        (22)

(SEQ ID NO. 23)
  SK* QMEEEAVRLFIEWLK* NGGPSSGAPPPS-NH₂        (23)

(SEQ ID NO. 24)
   K* QMEEEAVRLFIEWLK* NGGPSSGAPPPS-NH₂        (24)
``` where in the foregoing formulae (13) to (20),

*- indicates that an α-amino group at an N terminus is either protected by a protecting group or modified by a modifying group having no electric charge, and in the foregoing formulae (13) to (24), K* indicates that an amino group of a side chain of a lysine is protected by a protecting group, and —NH₂ indicates that a carboxyl group at a C-terminus is amidated;

[11] The method for producing the molecular probe for imaging of pancreatic islets according to [10], wherein the labeling of the precursor of the molecular probe for imaging of pancreatic islets includes labeling of the precursor with a labeling compound having a group represented by the following chemical formula (I) having an aromatic ring:

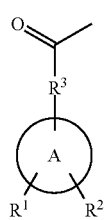

wherein

A represents either an aromatic hydrocarbon group or an aromatic heterocyclic group, $R^1$ represents a substituent that contains any one of $^{123}I$, $^{124}I$, $^{125}I$, and $^{131}I$, $R^2$ represents either a hydrogen atom, or one or more substituents different from that represented by $R^1$, and $R^3$ represents any one of a bond, a methylene group, and an oxymethylene group.

[12] A method for radioactively labeling a peptide having a plurality of amino acids having radioactively-labelable functional groups on side chains, the method comprising:

synthesizing a peptide using a protected amino acid in which an α-amino group at an N-terminus and a functional group of a side chain are protected by protecting groups;

deprotecting a functional group by removing a protecting group therefrom, wherein the functional group to be deprotected is a functional group that is not to be radioactively labeled, among the radioactively labelable functional groups of the side chains of the amino acids of the synthesized peptide;

protecting, again, the deprotected functional group of the side chain of the amino acid by a protecting group different from that removed upon the deprotecting;

deprotecting, by removing protecting groups, the other functional groups than the functional group of the side chain of the amino acid that is again protected, so as to obtain a peptide to be radioactively labeled;

radioactively labeling the obtained peptide with a labeling compound; and deprotecting the radioactively-labeled peptide by removing protecting groups.

[13] A method for producing a radioactively-labeled peptide, wherein the peptide has a plurality of amino acids having radioactively labelable functional groups on side chains, the method comprising:

synthesizing a peptide to be radioactively labeled, using protected amino acids in each of which an α-amino group at an N-terminus and a functional group of a side chain are protected by protecting groups;

deprotecting a functional group by removing a protecting group therefrom, wherein the functional group to be deprotected is a functional group that is not to be radioactively labeled, among the radioactively labelable functional groups of the side chains of the amino acids of the synthesized peptide;

protecting, again, the deprotected functional group of the side chain of the amino acid by a protecting group different from that removed upon the deprotecting;

deprotecting, by removing protecting groups, the other functional groups than the functional group of the side chain of the amino acid that is again protected, so as to obtain a peptide to be radioactively labeled;

radioactively labeling the obtained peptide with a labeling compound; and deprotecting the radioactively-labeled peptide by removing protecting groups.

[Imaging of Pancreatic Islets]

In the present specification, the "imaging of pancreatic islets" refers to "molecular imaging of pancreatic islets," and includes the imaging of in vivo spatial and/or time distribution of pancreatic islets. Further, in the present invention, the imaging of pancreatic islets preferably images pancreatic β-cells as target molecules, from the viewpoint of the prevention, treatment, and diagnosis of diabetes. Still further, in the present invention, the imaging of pancreatic islets is preferably noninvasive three-dimensional imaging, from the viewpoint of the quantification of the amount of pancreatic islets, and the application of this imaging to humans. The method of imaging is not limited particularly, if it is a method that enables noninvasive imaging of pancreatic islets. Examples of the method include methods utilizing positron emission tomography (PET), single photon emission computed tomography (SPECT), etc. Among these methods, PET and SPECT are preferred, from the viewpoint of quantifying the amount of pancreatic islets using the molecular probe of the present invention.

[Molecular Probe for Imaging of the Present Invention]

The molecular probe for imaging according to the present invention is a molecular probe for imaging of pancreatic islets including a polypeptide used in imaging of pancreatic islets, the polypeptide being represented by any one of the above-mentioned formulae (1) to (12). Preferably the molecular probe for imaging according to the present invention consists of any one of the following polypeptides: a polypeptide represented by any one of the above-mentioned formulae (1) to (12); a polypeptide obtained by deletion, insertion, or substitution of one to several amino acids with respect to a polypeptide represented by any one of the foregoing formulae (1) to (12), the polypeptide being capable of binding to pancreatic islets; and a polypeptide having a homology of 80% or higher with any one of the amino acid sequences of polypeptides represented by the foregoing formulae (1) to (12), the polypeptide being capable of binding to pancreatic islets.

Amino acid sequences of polypeptides of the foregoing formulae (1) to (12) are the amino acid sequences according to SEQ ID NOS. 1 to 12 shown in the Sequence Listing, respectively. Each of the following amino groups is labeled with a group represented by the chemical formula (I) above having an aromatic ring: the amino group of the side chain of a lysine at position 4 in the polypeptide of the formula (1) above; the amino group of the side chain of a lysine at position 3 in the polypeptide of the formula (2) above; the amino group of the side chain of a lysine at position 2 in the polypeptide of the formula (3) above; and the amino group of the side of a lysine at position 1 in polypeptide of the formula (4) above. Each of the following amino groups is labeled with a group represented by the formula (I) having an aromatic ring: the amino group of the side chain of a lysine at position 19 in the polypeptide of the formula (5) above; the amino group of the side chain of a lysine at position 18 in the polypeptide of the formula (6) above; the amino group of the side chain of a lysine at position 17 in the polypeptide of the formula (7) above; and the amino group of the side chain of a lysine at position 16 in the polypeptide of the formula (8) above. The α-amino group at an N-terminus of the polypeptide of each of the formulae (9) to (12) is labeled with a group represented by the chemical formula (I) having an aromatic ring. The α-amino group at an N-terminus of the polypeptide of each of the formulae (1) to (8) is either not modified, or is modified with a modification group having no electric charge. The carboxyl group at a C-terminus of the polypeptide of each of the formulae (1) to (12) is amidated with an amino group from the viewpoint of improving the affinity to the pancreatic β-cell.

Here, the amino acid sequences of the foregoing formula (1) (SEQ ID NO. 1 in the Sequence Listing) and the foregoing formula (5) (SEQ ID NO. 5 in the Sequence Listing) are identical to the amino acid sequence of exendin(9-39) except for the group represented by the chemical formula (I) above having an aromatic ring, which is bonded to the amino group of the side chain of a lysine, and the modifying group bondable to an α-amino group at an N-terminus. Further, the amino acid sequence of the foregoing formula (9) (SEQ ID NO. 9 in the Sequence Listing) is identical to the amino acid sequence of exendin(9-39) except for the group represented by the chemical formula (I) above having an aromatic ring, which is bonded to an α-amino group at an N-terminus. It is known that exendin(9-39) bonds to GLP-1R (glucagon-like peptide-1 receptor) expressed on the pancreatic β-cell. The molecular probe for imaging of pancreatic islets according to the present invention also is capable of binding to pancreatic islets, and preferably to the pancreatic β-cells.

In the present specification, the description of "being capable of binding to pancreatic islets" means the following: from the viewpoint of applying the present invention to the quantification of the pancreatic islets and a use of the examination and diagnosis, the molecular probe for imaging according to the present invention preferably is capable of binding to the pancreatic β-cells, more preferably is at least specific to the pancreatic β-cells in the pancreas, and further more preferably is at least specific to such an extent that a signal thereof does not overlap a signal of another organ/tissue in the signal detection in the noninvasive imaging with respect to humans.

In an another exemplary embodiment, the molecular probe for imaging according to the present invention includes a polypeptide used in imaging of pancreatic islets that is obtained by deletion, insertion, or substitution of one to several amino acids with respect to any one of the polypeptides of the foregoing formulae (1) to (12), and that is capable of binding to pancreatic islets. Here, exemplary ranges expressed by the foregoing description of "one to several" include the following ranges: 1 to 10; 1 to 9; 1 to 8; 1 to 7; 1 to 6; 1 to 5; 1 to 4; 1 to 3; 1 to 2; and 1. In the molecular probe for imaging according to this embodiment of the present invention, in the case of a polypeptide obtained by deletion, insertion, or substitution of one to several amino acids with respect to any one of the polypeptides of the foregoing formulae (1) to (8), it is preferable that the polypeptide includes one lysine labeled with a group represented by the chemical formula (I) above having an aromatic ring, that a carboxyl group at a C-terminus is amidated, and that the α-amino group at the N-terminus may be either not modified or modified by a modifying group having no electric charge. In the case where the polypeptide is a polypeptide that is obtained by deletion, insertion, or substitution of one to several amino acids with respect to any one of the polypeptides of the foregoing formulae (9) to (12), it is preferable that the α-amino group at a N-terminus is labeled with a group represented by the chemical formula (I) above having the aromatic ring and does not include any other labeling group, and further, that a carboxyl group at a C-terminus is amidated. Polypeptide obtained by deletion, insertion, or substitution of one to several amino acids with respect to a polypeptide represented by any one of the following formulae (1) to (12) preferably has a working effect identical to those of the polypeptides of the formulae (1) to (12), and more preferably has a working effect identical to those of the polypeptides of the formula (1) or the polypeptide of the formula (9).

In still another embodiment, the molecular probe for imaging according to the present invention may include a polypeptide used in imaging of pancreatic islets that has a homology of 80% or higher with any one of the amino acid sequences of polypeptides represented by the following formulae (1) to (12), and is capable of binding to pancreatic islets. Here, the "homology" may be any value calculated by an algorithm usually used by those skilled in the art, for example, BLAST or FASTA, or alternatively, it may be based on a value obtained by dividing the number of identical amino acid residues existing in two polypeptides compared, by the number of amino acids of an entire length of one of the polypeptides. Exemplary ranges of the homology may include the following ranges: not less than 85%; not less than 90%; and not less than 95%. In the molecular probe for imaging according to the present embodiment of the present invention, as well, in the case of a polypeptide having a homology of 80% or higher with any of the polypeptides of the formulae (1) to (8), the polypeptide preferably includes one lysine labeled with a group represented by the chemical formula (I) having an aromatic ring, and a carboxyl group at a C-terminus preferably is amidated, while an α-amino group at an N-terminus may be either not modified, or modified with a modifying group having no electric charge. In the case of a polypeptide having a homology of 80% or higher with an amino acid sequence of any of the polypeptides of the foregoing formulae (9) to (12), it is preferable that an α-amino group at an N-terminus is labeled with a group represented by the aforementioned chemical formula (I) having an aromatic ring, and does not have any other labeling group, and that a carboxyl group at a C-terminus is amidated. Polypeptide having homology of 80% or higher with any one of the amino acid sequences of polypeptides represented by the following formulae (1) to (12) preferably has a working effect identical to those of the polypeptides of the formulae (1) to (12), and more preferably has a working effect identical to that of the polypeptide of the formula (1) or the polypeptide of the formula (9).

The molecular probe for imaging of the present invention, as described above, can be used in imaging of pancreatic islets, and from the viewpoint of the application of the same to the examination and diagnosis for a human, preferably is used in noninvasive imaging of pancreatic islets, more preferably is used in imaging of pancreatic β-cells, and further preferably is used in imaging of GLP-1 receptor of pancreatic β-cells. From the same viewpoint, the molecular probe for imaging of the present invention preferably is used in imaging of pancreatic islets for quantifying the amount of the pancreatic islets, more preferably is used in imaging of pancreatic β-cells for quantifying the amount of the pancreatic islets, and further preferably is used in imaging of GLP-1 receptor of pancreatic β-cells for quantifying the amount of the pancreatic islets. Further, the molecular probe for imaging of pancreatic islets according to the present invention preferably is used in imaging of pancreatic islets for the prevention treatment or diagnosis of diabetes. Such imaging of pancreatic islets may be performed by, for example, PET or SPECT.

[Group to Label Amino Group of Side Chain of Lysine Residue or α-Amino Group at N-Terminus]

In the molecular probe for imaging of the present invention, the amino group of the side chain of the lysine residue represented by X in the amino acid sequences of the polypeptides of the aforementioned formulae (1) to (8), and the α-amino group at the N-terminus of each of the polypeptides of the aforementioned formulae (9) to (12), are labeled with groups represented by the following chemical formula (I) having an aromatic ring:

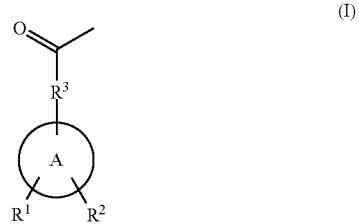

In the foregoing chemical formula (I), A represents an aromatic hydrocarbon group or an aromatic heterocyclic group. The aromatic hydrocarbon group preferably is an aromatic hydrocarbon group having 6 to 18 carbon atoms, and examples of the same include phenyl group, o-tolyl group, m-tolyl group, p-tolyl group, 2,4-xylyl group, p-cumenyl group, mesityl group, 1-naphthyl group, 2-naphthyl group, 1-anthryl group, 2-anthryl group, 9-anthryl group, 1-phenanthryl group, 9-phenanthryl group, 1-acenaphthyl group, 2-azulenyl group, 1-pyrenyl group, 2-triphenylenyl group, o-biphenylyl group, m-biphenylyl group, p-biphenylyl group, and terphenyl group. The aromatic heterocyclic group preferably is a 5 to 10-membered heterocyclic group having one or two of a nitrogen atom, an oxygen atom, or a sulfur atom, and examples of the same include triazolyl group, 3-oxadiazolyl group, 2-furyl group, 3-furyl group, 2-thienyl group, 3-thienyl group, 1-pyrrolyl group, 2-pyrrolyl group, 3-pyrrolyl group, 2-pyridyl group, 3-pyridyl group, 4-pyridyl group, 2-pyradyl group, 2-oxazolyl group, 3-isoxazolyl group, 2-thiazolyl group, 3-isothiazolyl group, 2-imidazolyl group, 3-pyrazolyl group, 2-quinolyl group, 3-quinolyl group, 4-quinolyl group, 5-quinolyl group, 6-quinolyl group, 7-quinolyl group, 8-quinolyl group, 1-isoquinolyl group, 2-quinoxalynyl group, 2-benzofuryl group, 2-benzothienyl group, N-indolyl group, and N-carbazolyl group. A preferably is, among these, phenyl group, triazolyl group, or pyridyl group, and more preferably, phenyl group.

In the aforementioned chemical formula (I), $R^1$ represents a substituent that contains any of $^{123}$I, $^{124}$I, $^{125}$I, and $^{131}$I. Examples of $R^1$ include [$^{123}$I] iodine atom, [$^{124}$I] iodine atom, [$^{125}$I] iodine atom, [$^{131}$I] iodine atom, [$^{123}$I] iodine atom-substituted $C_1$-$C_3$ alkyl groups, [$^{124}$I] iodine atom-substituted $C_1$-$C_3$ alkyl groups, [$^{125}$I] iodine atom-substituted $C_1$-$C_3$ alkyl groups, [$^{131}$I] iodine atom-substituted $C_1$-$C_3$ alkyl groups, iodine atom-substituted $C_1$-$C_3$ alkoxy groups, [$^{124}$I] iodine atom-substituted $C_1$-$C_3$ alkoxy groups, [$^{125}$I] iodine atom-substituted $C_1$-$C_3$ alkoxy groups, and [$^{131}$I] iodine atom-substituted $C_1$-$C_3$ alkoxy groups. In the present specification, the "$C_1$-$C_3$ alkyl group" refers to an alkyl group that has 1 to 3 carbon atoms, and examples of the same include methyl group, ethyl group, and propyl group. In the present specification, the "[$^{123}$I] iodine atom-substituted, [$^{124}$I] iodine atom-substituted, [$^{125}$I] iodine atom-substituted, or [$^{131}$I] iodine atom-substituted $C_1$-$C_3$ alkyl group" refers to an alkyl group that has 1 to 3 carbon atoms and in which one hydrogen atom is substituted with [$^{123}$I] iodine atom, [$^{124}$I] iodine atom, [$^{125}$I] iodine atom, or [$^{131}$I] iodine atom. In the present specification, the "$C_1$-$C_3$ alkoxy group" refers to an alkoxy group that has 1 to 3 carbon atoms, and examples of the same include methoxy group, ethoxy group, and propoxy group. In the present specification, the "[$^{123}$I] iodine atom-substituted, iodine atom-substituted, [$^{125}$I] iodine atom-substituted, or [$^{131}$I] iodine atom-substituted $C_1$-$C_3$ alkoxy group" refers to an alkoxy group that has 1 to 3 carbon atoms and in which one hydrogen atom is substituted with [$^{123}$I] iodine atom-substituted, [$^{124}$I] iodine atom-substituted, [$^{125}$I] iodine atom-substituted, or [$^{131}$I] iodine atom-substituted. From the viewpoint of performing PET, $R^1$ preferably is a substituent containing $^{124}$I that emits positron. From the viewpoint of performing SPECT, $R^1$ preferably is a substituent containing $^{123}$I or $^{125}$I that emits γ-rays. From the viewpoint of an amount of energy emitted, $R^1$ preferably is a substituent containing $^{123}$I. $R^1$ preferably is [$^{123}$I] iodine atom, [$^{124}$I] iodine atom, methyl [$^{123}$I] iodide group, methyl [$^{124}$I] iodide group, methoxy [$^{123}$I] iodide group, or methoxy [$^{124}$I] iodide group, and $R^1$ more preferably is [$^{123}$I] iodine atom, or [$^{124}$I] iodine atom. In $R^1$ in the aforementioned chemical formula (I), preferably a hydrogen atom at any one of an ortho-position, a meta-position, and a para-position is substituted, from the viewpoint of quantification, and more preferably, at a meta-position or a para-position.

In the aforementioned chemical formula (I), $R^2$ represents a hydrogen atom or one or more substituents different from that represented by $R^1$. $R^2$ may be a hydrogen atom or a substituent, but preferably, it is a hydrogen atom. In other words, in the aforementioned chemical formula (I), A preferably does not have a substituent other than $R^1$. In the case where $R^2$ represents a plurality of substituents, these substituents may be identical or different. Examples of the substituent include hydroxyl group, electron attractive groups, electron donative groups, $C_1$-$C_6$ alkyl groups, $C_2$-$C_6$ alkenyl groups, and $C_2$-$C_6$ alkynyl groups. Examples of the electron attractive group include cyano group, nitro group, halogen atoms, carbonyl group, sulfonyl group, acetyl group, and phenyl group. Examples of the halogen atom include fluorine atom, chlorine atom, bromine atom, and iodine atom. In the present specification, the "$C_1$-$C_6$ alkyl group" refers to an alkyl group having 1 to 6 carbon atoms, and examples of the same include methyl group, ethyl group, propyl group, isopropyl group, butyl group, isobutyl group, sec-butyl group, tert-butyl group, pentyl group, isopentyl group, and hexyl group. In the present specification, the "$C_2$-$C_6$ alkenyl group" refers to an alkenyl groups having 2 to 6 carbon atoms, and examples of the same include vinyl group, 1-propenyl group, 2-propenyl group, isopropenyl group, 1-butenyl group, 2-butenyl group, and 3-butenyl group. In the present specification, the "$C_2$-$C_6$ alkynyl group" refers to an alkynyl group having 2 to 6 carbon atoms, and examples of the same include ethynyl group, 1-propynyl group, 2-propynyl group, 1-butynyl group, 2-butynyl group, and 3-butynyl group. Among these, the substituent preferably is hydroxyl group or an electron attractive group.

In the aforementioned chemical formula (I), $R^3$ represents any one of a bond, a methylene group, and an oxymethylene group. Among these, a bond or a methylene group is preferred, and a bond is preferred further.

In the molecular probe for imaging according to the present invention, the group represented by the chemical formula (I) above having an aromatic ring preferably is the group represented by the chemical formula (II) below. In the chemical formula (II) below, $R^1$ is as described above.

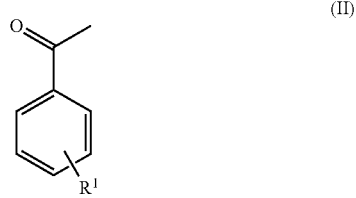

(II)

[Modifying Group]

In the molecular probe for imaging of the present invention, an α-amino group at an N-terminus in any one of the polypeptides of the above-described formulae (1) to (8) may be modified with a modifying group having no electric charge, from the viewpoint of canceling a positive charge of the α-amino group at the N-terminus thereby suppressing accumulation in kidneys of the molecular probe for imaging the present invention. Examples of such a modifying group having no electric charge include 9-fluorenylmethyloxycarbonyl group (Fmoc), tert-butoxycarbonyl group (Boc), benzyloxycarbonyl group (Cbz), 2,2,2-trichloroethoxycarbonyl group (Troc), allyloxycarbonyl group (Alloc), 4-methoxytrityl group (Mmt), amino group, alkyl groups having 3 to 20 carbon atoms, 9-fluoreneacetyl group, 1-fluorenecarboxylic acid group, 9-fluorenecarboxylic acid group, 9-fluorenone-1-carboxylic acid group, benzyloxycarbonyl group, xanthyl group (Xan), trityl group (Trt), 4-methyltrityl group (Mtt), 4-methoxy2,3,6-trimethyl-benzenesulfonyl group (Mtr), mesitylene-2-sulfonyl group (Mts), 4,4-dimethoxybenzohydryl group (Mbh), tosyl group (Tos), 2,2,5,7,8-pentamethyl-chroman-6-sulfonyl group (Pmc), 4-methylbenzyl group (MeBzl), 4-methoxybenzyl group (MeOBzl), benzyloxy group (BzlO), benzyl group (Bzl), benzoyl group (Bz), 3-nitro-2-pyridinesulfenyl group (Npys), 1-(4,4-dimethyl-2,6-diaxocyclohexylidene)ethyl group (Dde), 2,6-dichlorobenzyl group (2,6-DiCl-Bzl), 2-chlorobenzyloxycarbonyl group (2-Cl-Z), 2-bromobenzyloxycarbonyl group (2-Br-Z), benzyloxymethyl group (Born), cyclohexyloxy group (cHxO), t-butoxymethyl group (Burn), t-butoxy group (tBuO), t-butyl group (tBu), acetyl group (Ac), trifluoroacetyl group (TFA), o-bromobenzyloxycarbonyl group, t-butyldimethylsilyl group, 2-chlorobenzyl (Cl-z) group, cyclohexyl group, cyclopentyl group, isopropyl group, pivalyl group, tetrahydropyran-2-yl group, and trimethylsilyl group. Among these, preferably, the modifying group is acetyl group, benzyl group, benzyloxymethyl group, o-bromobenzyloxycarbonyl group, t-butyl group, t-butyldimethylsilyl group, 2-chlorobenzyl group, 2,6-dichlorobenzyl group, cyclohexyl group, cyclopentyl group, isopropyl group, pivalyl group, tetrahydropyran-2-yl group, tosyl group, trimethylsilyl group, or trityl group. More preferably, the modifying group is acetyl group.

[Imaging Method]

Another aspect of the present invention relates to a method for imaging of pancreatic islets that includes imaging pancreatic islets using the molecular probe for imaging of the present invention. Still another aspect of the present invention relates to a method for imaging of pancreatic islets that includes detecting a signal of the molecular probe for imaging of the present invention from an analyte to which the molecular probe has been administered, or detecting a signal of the molecular probe for imaging of the present invention that has been bound to pancreatic islets preliminarily. In the imaging method, (i) a signal of the molecular probe for imaging of the present invention where the molecular probe has been administered to an analyte in an enough amount for imaging, or (ii) a signal of the molecular probe for imaging of the present invention where an enough amount for imaging has been bound to pancreatic islets preliminarily is detected preferably. The imaging of pancreatic islets is as described above. The method for imaging islets according to the present invention preferably is a method for imaging pancreatic β-cells from the viewpoint of the application of the same to the examination and diagnosis.

The detection of a signal of a molecular probe for imaging of the present invention can be performed by, for example, the determination by means of PET and/or the determination by means of SPECT. The determination by means of PET and the determination by means of SPECT include, for example, photographing an image, and determining an amount of pancreatic islets. The method for imaging of the present invention may include reconfiguring the detected signal so as to convert the same into an image, and further may include displaying the image.

The determination by means of SPECT includes, for example, determining, with use of a gamma camera, γ-rays emitted from a subject having (i) pancreatic islets to which the molecular probe of the present invention has been bound preliminarily or (ii) an analyte to which the molecular probe of the present invention has been administered. The determination with use of the gamma camera includes, for example, measuring radiation (γ-rays) emitted from the radioactive iodine used for labeling the molecular probe for imaging of the present invention during a certain time unit, and preferably includes determining a direction in which the radiation is emitted and a radiation dose during a certain time unit. The method for imaging according to the present invention further may include presenting the determined distribution of the molecular probe for imaging of the present invention obtained by the measurement of the radiation as a cross-sectional image, and reconfiguring the obtained cross-sectional image. Examples of the subject (analyte) include humans and/or mammals other than humans.

The determination by means of PET include, for example, simultaneously measuring a pair of annihilation radiations generated upon the coupling between a positron and an electron, with use of a detector for PET, from a subject having (i) pancreatic islets to which the molecular probe of the present invention has been bound preliminarily or (ii) an analyte to which the molecular probe of the present invention has been administered, and further may include figuring a three-dimensional distribution of positions of radioactive iodine emitting positrons, based on the measurement results.

In the method for imaging according to the present invention, the determination by means of X-ray CT or MRI may be performed, together with the determination by means of SPECT or the determination by means of PET. This makes it possible to obtain, for example, a fusion image obtained by fusion of an image obtained by SPECT or an image obtained by PET (functional image), with an image obtained by CT or an image obtained by MRI (morphological image).

The method for imaging of the present invention may include determining a state of pancreatic islets based on the results of the imaging of pancreatic islets with use of the molecular probe for imaging of the present invention. Determining a state of pancreatic islets based on the results of the imaging of pancreatic islets with use of the molecular probe includes, for example, determining the presence/absence of pancreatic islets by analyzing an image of the imaging of pancreatic islets, and determining an increase/decrease in the amount of pancreatic islets.

The method for imaging of the present invention may include administering the molecular probe for imaging of the present invention to a subject, and it is preferable to administer the molecular probe for imaging of the present invention in an enough amount for obtaining a desired contrast for imaging. The detection of a signal of the molecular probe for imaging of the present invention preferably is carried out after a certain lapse of time since the administration of the molecular probe. Examples of the subject include humans and/or mammals other than humans. The administration to a subject may be local administration or systemic administration. A path for administration may be determined appropriately according to a state of a subject and the like, and it may be, for example, intravenous, intraarterial, intradermal, and intraabdominal injection or infusion. The molecular probe for imaging of the present invention preferably is administered together with a carrier. Examples usable as the carrier include aqueous solvents and non-aqueous solvents. Examples of the aqueous solvent include potassium phosphate buffer solution, physiologic saline, Ringer's solution, and distilled water. Examples of the non-aqueous solvent include polyethylene glycol, vegetable fats and oils, ethanol, glycerol, dimethyl sulfoxide, and propylene glycol. The amount of the molecular probe of the present invention for imaging of pancreatic islets or for determining an amount of pancreatic islets may be set to be, for example, not more than 1 μg. The time period from the administration to the determination may be decided appropriately according to, for example, a time that the molecular probe takes to bind to pancreatic islets, the type of the molecular probe, the decomposition time of the molecular probe, etc.

[Method for Determining Amount of Pancreatic Islets]

Still another aspect of the present invention relates to a method for determining an amount of pancreatic islets, including detecting a signal of the molecular probe for imaging of the present invention that has been bound to pancreatic islets preliminarily, and calculating an amount of the pancreatic islets from the detected signal of the molecular probe. The method for determining an amount of pancreatic islets according to the present invention may include performing imaging of pancreatic islets using the molecular probe for imaging of the present invention. The imaging of pancreatic islets is as described above. The calculation of an amount of pancreatic islets from results of imaging of pancreatic islets using the molecular probe may be performed by, for example, analyzing an image obtained by imaging of pancreatic islets. The quantification of a subject of the imaging from results of the imaging can be performed easily by any person skilled in the art, using a calibration curve, an appropriately program, or the like. The method for determining an amount of pancreatic islets according to the present invention preferably is a method for determining an amount of pancreatic β-cells from the viewpoint of the application of the same to the examination and diagnosis.

Still another aspect of the present invention relates to a method for determining an amount of pancreatic islets, including detecting a signal of the molecular probe for imaging of the present invention from an analyte to which the molecular probe for imaging of the present invention has been administered and/or a signal of the molecular probe for imaging of the present invention that has been bound to pancreatic islets preliminarily, and calculating an amount of the pancreatic islets from the detected signal of the molecular probe for imaging.

The method for determining an amount of pancreatic islets according to the present invention may include presenting the calculated amount of pancreatic islets. Presenting the calculated amount of pancreatic islets includes, for example, storing the calculated amount of pancreatic islets or outputting the same to the outside. Outputting the same to the outside includes, for example, displaying the same on a monitor and printing the same.

[Methods for Prevention, Treatment, and Diagnosis of Diabetes]

Still another aspect of the present invention relates to a method for prevention, treatment, or diagnosis of diabetes. As described above, in the diabetes developing process, the amount of pancreatic islets (particularly, the amount of pancreatic βcells) is decreased prior to the occurrence of glucose tolerance abnormalities. Therefore, when functional abnormalities are detected or there are subjective symptoms, diabetes has already reached the stage where it is too difficult to be treated. With the imaging method using the molecular probe for imaging of the present invention and/or the method for determining an amount of the pancreatic islets using the same, however, a decrease in the amount of the pancreatic islets and/or the amount of the pancreatic β-cells can be detected at an early stage, and further, new methods for prevention, treatment, and diagnosis of diabetes can be created. Examples of a subject on which prevention, treatment, and diagnosis of diabetes is carried out include humans and/or mammals other than humans.

A method for diagnosis of diabetes according to the present invention may include performing imaging of pancreatic islets with use of the molecular probe for imaging of the present invention, determining a state of the pancreatic islets based on the obtained image of the pancreatic islets or the obtained amount of the pancreatic islets, and performing diagnosis of diabetes based on the determination results. The determination of a state of pancreatic islets includes, for example, determining an increase/decrease, or a change, in the amount of pancreatic islets by comparing the obtained image of pancreatic islets with an image of pancreatic islets as a reference, or comparing the obtained amount of pancreatic islets with an amount of pancreatic islets as a reference. Further, the determination of a state of pancreatic islets may be carried out using an information processing device. When it is determined that the amount of pancreatic islets has decreased, preferably this information is presented, and when it is determined that the amount of pancreatic islets has increased or has been maintained, preferably this information is presented. The diagnosis of diabetes on the basis of the determination results includes, for example, determining a risk of development of diabetes, judging it to be diabetes, and determining a degree of development of diabetes.

A method for treatment of diabetes of the present invention includes performing imaging of pancreatic islets with use of the molecular probe for imaging of the present invention, determining a state of pancreatic islets on the basis of the obtained image of the pancreatic islets or the obtained amount of the pancreatic islets so as to perform diagnosis of diabetes, and treating diabetes on the basis of the diagnosis. The determination of a state of pancreatic islets and the diagnosis of diabetes can be performed in the same manner as those in the method for diagnosis of diabetes according to the present invention. The method for treatment of diabetes according to the present invention may include evaluating an effect of treatment such as medication and diet performed on a subject, focusing on a change in an amount of pancreatic islets.

A method for prevention of diabetes of the present invention includes performing imaging of pancreatic islets with use of the molecular probe for imaging of the present invention, and determining a state of pancreatic islets on the basis of the obtained image of the pancreatic islets or the obtained amount of the pancreatic islets so as to determine a risk of development of diabetes. The method for prevention of diabetes of the present invention may include regularly determining an amount of pancreatic islets, and checking presence/absence of a tendency of a decrease in the amount of pancreatic islets.

Still another preferable aspect of the present invention relates to a method for ultra-early diagnosis of diabetes. The method for ultra-early diagnosis of diabetes of the present invention may include, for example, imaging pancreatic islets or determining an amount of pancreatic islets by the method of the present invention in comprehensive or ordinary medical examination, and determining a state of the pancreatic islets on the basis of the obtained image of the pancreatic islets or the determined amount of the pancreatic islets. Further, a method for treatment of diabetes of the present invention may include imaging pancreatic islets and/or determining an amount of pancreatic islets by the method of the present invention, and evaluating functional recovery of the pancreatic islets on the basis of the obtained image of the pancreatic islets and/or the determined amount of the pancreatic islets.

[Kit of the Present Invention]

Still another aspect of the present invention also relates to a kit including the molecular probe for imaging of the present invention. Examples of embodiments of the kit of this aspect include a kit for performing the imaging method of the present invention, a kit for performing the method for determining an amount of pancreatic islets according to the present invention, and a kit for prevention, treatment, or diagnosis of diabetes according to the present invention. Preferably, in each of these embodiments, the kit includes an instruction manual suitable for the embodiment.

In the kit of the present invention, the molecular probe for imaging of the present invention included in the kit preferably is in a form of a parenteral solution. Therefore, the kit of the present invention preferably includes a parenteral solution that contains the molecular probe for imaging of the present invention. The parenteral solution may contain the molecular probe for imaging of the present invention as an effective ingredient, and further, for example, a medicinal additive such as a carrier. In the present specification, the "medicinal additive" refers to a compound that has obtained authorization as a medicinal additive in the Japanese, U.S. and/or European pharmacopoeias. Examples of the carrier include aqueous solvents and non-aqueous solvents. Examples of the aqueous solvent include potassium phosphate buffer solution, physiologic saline, Ringer's solution, and distilled water. Examples of the non-aqueous solvent include polyethylene glycol, vegetable fats and oils, ethanol, glycerol, dimethyl sulfoxide, and propylene glycol. The kit of the present invention further may include a container for containing the molecular probe for imaging of the present invention, and the container may be filled with the molecular probe for imaging of the present invention or a parenteral solution that contains the molecular probe for imaging of the present invention. Examples of the container include a syringe and a vial.

The kit of the present invention may further include, for example, a component used for preparing a molecular probe, such as a buffer or an osmotic regulator, and an instrument used in administration of a molecular probe, such as a syringe.

[Reagent for Imaging of the Present Invention]

Still another aspect of the present invention relates to a reagent for imaging that contains the molecular probe for imaging of the present invention. The reagent for imaging according to the present invention may contain the molecular probe for imaging of the present invention as an effective ingredient, and further, a medicinal additive such as a carrier. The carrier is as described above.

[Method for Preparation of Molecular Probe for Imaging of the Present Invention]

The molecular probe for imaging according to the present invention can be prepared by labeling a molecular probe precursor containing a polypeptide represented by any one of the formulae (13) to (24) below with a labeling compound having a group represented by the chemical formula (I) above having an aromatic ring, and thereafter deprotecting the molecular probe precursor by removing a protecting group. Through this labeling operation, an amino group of a side chain of a lysine to which no protecting group is bonded, or an α-amino group at an N-terminus to which no protecting group or modifying group is not bonded, can be labeled.

```
*-DLSKQMEEEAVRLFIEWLK* NGGPSSGAPPPS-NH2         (SEQ ID NO. 13)
                                                        (13)

*-LSKQMEEEAVRLFIEWLK* NGGPSSGAPPPS-NH2          (SEQ ID NO. 14)
                                                        (14)

*-SKQMEEEAVRLFIEWLK* NGGPSSGAPPPS-NH2           (SEQ ID NO. 15)
                                                        (15)

*-KQMEEEAVRLFIEWLK* NGGPSSGAPPPS-NH2            (SEQ ID NO. 16)
                                                        (16)

*-DLSK* QMEEEAVRLFIEWLKNGGPSSGAPPPS-NH2         (SEQ ID NO. 17)
                                                        (17)

*-LSK* QMEEEAVRLFIEWLKNGGPSSGAPPPS-NH2          (SEQ ID NO. 18)
                                                        (18)

*-SK* QMEEEAVRLFIEWLKNGGPSSGAPPPS-NH2           (SEQ ID NO. 19)
                                                        (19)

*-K* QMEEEAVRLFIEWLKNGGPSSGAPPPS-NH2            (SEQ ID NO. 20)
                                                        (20)

DLSK* QMEEEAVRLFIEWLK* NGGPSSGAPPPS-NH2         (SEQ ID NO. 21)
                                                        (21)

LSK* QMEEEAVRLFIEWLK* NGGPSSGAPPPS-NH2          (SEQ ID NO. 22)
                                                        (22)

SK* QMEEEAVRLFIEWLK* NGGPSSGAPPPS-NH2           (SEQ ID NO. 23)
                                                        (23)

K* QMEEEAVRLFIEWLK* NGGPSSGAPPPS-NH2            (SEQ ID NO. 24)
                                                        (24)
``` where in the foregoing formulae (13) to (20),

*- indicates that an α-amino group at an N terminus is either protected by a protecting group or modified by a modifying group having no electric charge, in the foregoing formulae (13) to (24), K* indicates that an amino group of a side chain of a lysine is protected by a protecting group, and —NH2 indicates that a carboxyl group at a C-terminus is amidated.

The molecular probe precursor of the present invention can be synthesized by peptide synthesis in accordance with a typical method such as the Fmoc method, and the peptide synthesis method is not limited particularly.

[Protecting Group]

The protecting group is intended to protect the other amino group of the molecular probe precursor than a specific amino group of the molecular probe for imaging according to the present invention while the specific amino group is being labeled, and a known protecting group that can perform such a function can be used. As the protecting group, any known protecting group capable of performing such a function can be used. The protecting group is not limited particularly, and examples of the same include 9-fluorenylmethyloxycarbonyl group (Fmoc), tert-butoxycarbonyl group (Boc), benzyloxycarbonyl group (Cbz), 2,2,2-trichloroethoxycarbonyl group (Troc), allyloxycarbonyl group (Alloc), 4-methoxytrityl group (Mmt), amino group, alkyl groups having 3 to 20 carbon atoms, 9-fluoreneacetyl group, 1-fluorenecarboxylic acid group, 9-fluorenecarboxylic acid group, 9-fluorenone-1-carboxylic acid group, benzyloxycarbonyl group, xanthyl group (Xan), trityl group (Trt), 4-methyltrityl group (Mtt), 4-methoxy2,3,6-trimethyl-benzenesulfonyl group (Mtr), mesitylene-2-sulfonyl group (Mts), 4,4-dimethoxybenzohydryl group (Mbh), tosyl group (Tos), 2,2,5,7,8-pentamethyl-chroman-6-sulfonyl group (Pmc), 4-methylbenzyl group (MeBzl), 4-methoxybenzyl group (MeOBzl), benzyloxy group (BzlO), benzyl group (Bzl), benzoyl group (Bz), 3-nitro-2-pyridinesulfenyl group (Npys), 1-(4,4-dimethyl-2,6-diaxocyclohexylidene)ethyl group (Dde), 2,6-dichlorobenzyl group (2,6-DiCl-Bzl), 2-chlorobenzyloxycarbonyl group (2-Cl-Z), 2-bromobenzyloxycarbonyl group (2-Br-Z), benzyloxymethyl group (Bom), cyclohexyloxy group (cHxO), t-butoxymethyl group (Bum), t-butoxy group (tBuO), t-butyl group (tBu), acetyl group (Ac), and trifluoroacetyl group (TFA). From the viewpoint of handleability, Fmoc or Boc is preferred. The deprotecting methods with respect to these protecting groups are known, and any person skilled in the art is able to perform the deprotecting appropriately.

The labeling can be performed using a labeling compound having a group represented by the foregoing chemical formula (I) having an aromatic ring. The labeling compound used in the labeling preferably is a succinimidyl ester compound in which the group represented by the foregoing chemical formula (I) is bonded with succinimide via ester bond, more preferably, a succinimidyl ester compound represented by the chemical formula (III) shown below, and further more preferably, a succinimidyl ester compound represented by the chemical formula (IV) shown below. In the chemical formula (III) below, A, $R^1$, $R^2$, and $R^3$ represent the same as those in the case of the foregoing chemical formula (I). In the chemical formula (IV) below, $R^1$ represents the same as that in the case of the foregoing chemical formula (I).

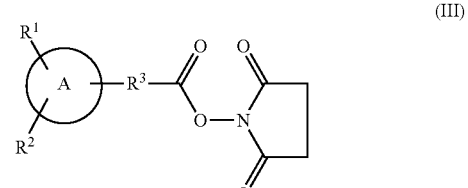
(III)

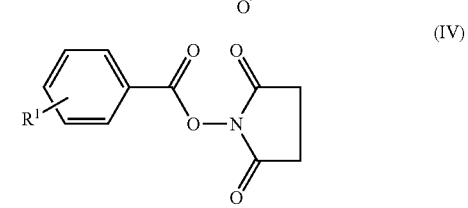
(IV)

A labeling compound used in the labeling preferably in particular is [$^{123}$I]N-succinimidyl 3-iodobenzoate, [$^{124}$I]N-succinimidyl 3-iodobenzoate, or [$^{131}$I]N-succinimidyl 3-iodobenzoate, in which $R^1$ in the foregoing chemical formula (IV) is [$^{123}$I]iodine atom, [$^{124}$I]iodine atom, or [$^{131}$I]iodine atom, respectively.

Still another aspect of the present invention relates to a method for producing a molecular probe for imaging according to the present invention, comprising labeling and deprotecting the molecular probe precursor for imaging. In the method for producing the molecular probe for imaging according to the present invention, the molecular probe precursor for imaging preferably consists of any one of the following polypeptides:

a polypeptide represented by any one of the formulae (13) to (24) above;

a polypeptide obtained by deletion, insertion, or substitution of one to several amino acids with respect to a polypeptide represented by any one of the formulae (13) to (24) above, the polypeptide being capable of binding to pancreatic islets after being labeled and deprotected; and a polypeptide having a homology of 80% or higher with any one of the amino acid sequences of polypeptides represented by the formulae (13) to (24) above, the polypeptide being capable of binding to pancreatic islets after being labeled and deprotected.

In the method for producing a molecular probe for imaging according to the present invention, the labeling of the molecular probe precursor for imaging preferably includes the labeling with a labeling compound including a group represented by the following chemical formula (I) having an aromatic ring:

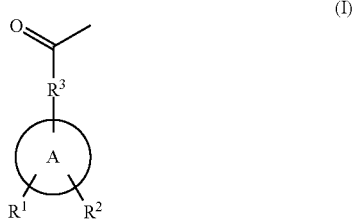

(I)

where A, $R^1$, $R^2$, and $R^3$ are as described above. The labeling compound having the group represented by the foregoing chemical formula (I) above having an aromatic ring preferably is a succinimidyl ester compound in which the group represented by the chemical formula (I) above is bonded with succinimide via ester bond, more preferably, a succinimidyl ester compound represented by the chemical formula (III) mentioned above, and further more preferably, a succinimidyl ester compound represented by the chemical formula (IV) mentioned above.

In the method for producing a molecular probe for imaging of pancreatic islets according to the present invention, the synthesis of a labeling compound having a group represented by the chemical formula (I) above having an aromatic ring may be carried out by an automatic synthesizing device. Alternatively, both of the following may be carried out by a single automatic synthesizing device: the synthesis of the labeling compound having the group represented by the foregoing chemical formula (I) having an aromatic ring; and the labeling and deprotecting of a molecular probe precursor for imaging in which the foregoing labeling compound is used.

Examples of the above-described molecular probe precursor include a precursor of a molecular probe for imaging that can be a precursor for the molecular probe for imaging of the present invention, wherein the precursor consists of any one of the following polypeptides: a polypeptide obtained by deletion, insertion, or substitution of one to several amino acids with respect to a polypeptide represented by any one of the following formulae (13) to (24), the polypeptide being capable of binding to pancreatic islets after being labeled and deprotected; and a polypeptide having a homology of 80% or higher with any one of the amino acid sequences of polypeptides represented by the following formulae (13) to (24), the polypeptide being capable of binding to pancreatic islets after being labeled and deprotected.

Therefore, still another aspect of the present invention provides a molecular probe precursor for imaging of pancreatic islets, consisting of any one of the following polypeptides: a polypeptide represented by any one of the formulae (13) to (24) above; a polypeptide obtained by deletion, insertion, or substitution of one to several amino acids with respect to a polypeptide represented by any one of the formulae (13) to (24) above, the polypeptide being capable of binding to pancreatic islets after being labeled and deprotected; and a polypeptide having a homology of 80% or higher with any one of the amino acid sequences of polypeptides represented by the formulae (13) to (24) above, the polypeptide being capable of binding to pancreatic islets after being labeled and deprotected. With use of the molecular probe precursor for imaging according to the present invention, including the polypeptide of any one of the formulae (13) to (24) above, an effect of easily providing the molecular probe for imaging according to the present invention can be achieved.

[Another Aspect of the Kit of the Present Invention]

Still another aspect of the present invention relates to a kit including the aforementioned molecular probe precursor for imaging. Exemplary embodiments of the kit including the molecular probe precursor for imaging according to the present invention include a kit for preparing the molecular probe for imaging according to the present invention, a kit for performing the method for imaging of the present invention, a kit for performing the method for determining an amount of pancreatic islets according to the present invention, and a kit for prevention, treatment, or diagnosis of diabetes according to the present invention. Preferably, in each of these embodiments, the kit including the molecular probe precursor for imaging according to the present invention includes an instruction manual suitable for each embodiment.

The kit including the molecular probe precursor for imaging may include, for example, a labeling compound used in the labeling of the precursor of the molecular probe for imaging, the labeling compound having the group represented by the aforementioned chemical formula (I) having an aromatic ring. The labeling compound having the group represented by the chemical formula (I) having an aromatic ring preferably is a succinimidyl ester compound in which the group represented by the foregoing chemical formula (I) is bonded with succinimide via ester bond, more preferably, a succinimidyl ester compound represented by the aforementioned chemical formula (III), and further more preferably, a succinimidyl ester compound represented by the aforementioned chemical formula (IV). The kit of the present embodiment more preferably includes, in particular, [$^{123}$I]N-succinimidyl 3-iodobenzoate, [$^{124}$I]N-succinimidyl 3-iodobenzoate, or [$^{131}$I]N-succinimidyl 3-iodobenzoate as the labeling compound. The kit of the present embodiment further may include, for example, an instruction manual that describes the method for labeling the precursor of the molecular probe for imaging of the present invention in which the above-described labeling compound is used.

The kit including the molecular probe precursor for imaging preferably further includes a starting material for the above-described labeling compound. Examples of the starting material include 2,5-dioxopyrrolidin-1-yl 3-(tributylstannyl)benzoate.

The kit including the molecular probe precursor for imaging further may include, for example, a reagent to be used for deprotecting the molecular probe precursor for imaging and/or a reagent to be used for the labeling.

The kit including the molecular probe precursor for imaging further may include, for example, an automatic synthesizing device for synthesizing the labeling compound, and an instruction manual that describes a method for synthesizing the labeling compound having a group represented by the aforementioned chemical formula (I) having an aromatic ring, using the foregoing automatic synthesizing device for synthesizing the labeling compound. The automatic synthesizing device may be capable of synthesizing the labeling compound, and further, for example, capable of labeling and deprotecting the precursor of the molecular probe for imaging in which the synthesized labeling compound is used. The kit further may include, for example, a reagent containing a radioactive iodine to be used in synthesizing the labeling compound. Examples of the reagent containing a radioactive iodine include reagents containing radioactive isotopes such as $^{123}$I, $^{124}$I, $^{125}$I, and $^{131}$I.

Still another aspect of the present invention relates to a kit that includes an automatic peptide synthesizing device for synthesizing the molecular probe precursor for imaging, and the labeling compound having the group represented by the aforementioned chemical formula (I) having an aromatic ring, and/or an automatic synthesizing device for synthesizing the labeling compound. The automatic synthesizing device may be capable of synthesizing the labeling compound, and further, for example, capable of labeling and deprotecting the molecular probe precursor for imaging in which the synthesized labeling compound is used. The kit may include an instruction manual that describes a method for synthesizing the molecular probe precursor for imaging. The instruction manual further may describe, for example, a method for synthesizing the labeling compound having a group represented by the aforementioned chemical formula (I) having an aromatic ring, a labeling method using the same, and a deprotecting method using the same. The kit further may include a reagent containing radioactive iodine to be used in synthesis of a labeling compound.

Still another aspect of the present invention relates to a kit that includes the following: an automatic synthesizing device that performs the synthesis of the molecular probe precursor for imaging, the synthesis of the aforementioned labeling compound, and the labeling and deprotecting of the aforementioned molecular probe precursor for imaging in which the aforementioned labeling compound is used; and an instruction manual that describes a method for producing a molecular probe for imaging of the present invention with use of the foregoing automatic synthesizing device. The instruction manual preferably describes, for example, a method for synthesizing the molecular probe precursor, a method for synthesizing the aforementioned labeling compound, and a method for labeling and deprotecting the molecular probe precursor for imaging in which the aforementioned labeling compound is used. The kit further may include a reagent containing radioactive iodine to be used in synthesis of the labeling compound.

[Method for Labeling a Peptide According to the Present Invention]

Still another aspect of the present invention relates to a method for labeling a peptide. The method for labeling a peptide according to the present invention is a method for radioactively labeling a peptide having a plurality of amino acids having radioactively-labelable functional groups on side chains, and the method includes: synthesizing a peptide using protected amino acids in which an α-amino group at an N-terminus and a functional group of a side chain are protected by protecting groups; deprotecting a functional group by removing a protecting group therefrom, the functional group to be deprotected being a functional group that is not to be radioactively labeled, among the radioactively labelable functional groups of the side chains of the amino acids of the synthesized peptide; protecting, again, the deprotected functional group of the side chain of the amino acid by a protecting group different from that removed upon the deprotecting; deprotecting, by removing protecting groups, the other functional groups than the functional group of the side chain of the amino acid that is again protected, so as to obtain a peptide to be radioactively labeled; radioactively labeling the obtained peptide with a labeling compound; and deprotecting the radioactively-labeled peptide by removing protecting groups.

The method for labeling a peptide according to the present invention, as another aspect thereof, relates to a method for labeling a peptide, the method including the steps of peptide synthesis; substitution of protecting group; deprotection by removing protecting groups; and radioactive labeling.

The step of peptide synthesis include synthesizing a peptide using protected amino acids, and the protected amino acids are selected from the group consisting of a protected amino acid in which an α-amino group at an N-terminus is protected by a protecting group X; a protected amino acid in which an α-amino group at an N-terminus is protected by a protecting group X and a functional group a of a side chain is protected by a protecting group Y1; a protected amino acid in which an α-amino group at an N-terminus is protected by a protecting group X and a functional group b of a side chain is protected by a protecting group Y2; and a protected amino acid in which an α-amino group at an N-terminus is protected by a protecting group X and a functional group c of a side chain is protected by a protecting group Y3. The functional group a is a functional group of a side chain of an amino acid to be radioactively labeled, the functional group b is a radioactively-labelable functional group of a side chain of an amino acid that is not to be radioactively labeled, and the functional group c is a functional group of a side chain of an amino acid other than the functional group a and the functional group b.

The step of substitution of a protecting group includes deprotecting the functional group b by removing the protecting group Y2, and thereafter protecting the functional group b by a protecting group Z different from the protecting group Y2. The step preferably includes deprotecting the functional group b by removing the protecting group Y2 without deprotecting the functional groups a and c, and thereafter protecting the functional group b by a protecting group Z different from the protecting group Y2.

The step of deprotection by removing protecting groups include deprotecting the functional groups a and c by removing the protecting groups Y1 and Y3, respectively. The step preferably includes deprotecting the functional groups a and c by removing the protecting groups Y1 and Y3, respectively, without deprotecting the functional group b.

The step of radioactive labeling includes radioactively labeling the functional group a of the peptide after the step of deprotection, using a radioactive labeling compound, and deprotecting the functional group b and the α-amino group at the N-terminus by removing the protecting group Z and the protecting group X, respectively.

In the labeling method of the present invention, the radioactive labeling of a peptide with a labeling compound is performed to the peptide in a state in which a radioactively-labelable functional group (functional group b) of a side chain of an amino acid other than a functional group to be radioactively labeled (functional group a) is protected by a protecting group (protecting group Z). More specifically, in the labeling method of the present invention, the radioactive labeling of a peptide with a labeling compound is performed to a peptide in a state in which the functional group b is protected again by the protecting group Z after the protecting group Y2 is removed, while the functional group a to be radioactively labeled is deprotected. Therefore, with the labeling method of the present invention, it is possible to selectively label an intended functional group (functional group a) alone. With the labeling method of the present invention, it is possible to improve the labeling efficiency, and to improve the yield of a desired peptide that is radioactively labeled.

[Peptide Synthesis]

The peptide synthesis is conducted by a peptide synthesizing method using protected amino acids in which an α-amino group at an N-terminus and/or a functional group of a side chain (functional group a, b, or c) are protected by protecting groups.

The peptide synthesis can be carried out by, for example, a known organic-chemical peptide synthesis method. For example, the peptide synthesis can be carried out according to the descriptions in "*Seikagaku Jikken Koza*" ("Biochemical Experiment Seminar") edited by the Japanese Biochemical Society, Vol. 1, "Protein IV", pages 207 to 495 (published by Tokyo Kagaku Dojin, 1977), and "*Shin Seikagaku Jikken Koza*" ("New Biochemical Experiment Seminar") edited by the Japanese Biochemical Society, Vol. 1, "Protein VI", pages 3 to 74 (published by Tokyo Kagaku Dojin, 1992), etc.

Examples of the organic-chemical peptide synthesis method include the peptide solid-phase synthesis method, and the peptide liquid-phase synthesis method, among which the peptide solid-phase synthesis method is preferred. In the present specification, the "peptide solid-phase synthesis method" refers to a method in which a C-terminus of an amino acid or a peptide is fixed to a solid-phase carrier via a linker, and amino acids are extended one by one toward an N-terminus. Examples of the peptide solid-phase synthesis method include the Fmoc method and the Boc method, among which the Fmoc method is preferred. In the present specification, the "Fmoc method" refers to a method wherein amino acids in which the α-amino group at the N-terminus is protected by Fmoc (9-fluorenylmethyloxycarbonyl group) are used, and they are condensed, so as to synthesize a peptide. More specifically, an amino acid corresponding to a C-terminus of a peptide to be synthesized, or a peptide including an amino acid corresponding to the C-terminus of a peptide to be synthesized, is bonded to a solid-phase carrier such as a resin, the deprotection of an α-amino group at a N-terminus by removing the Fmoc group as a protecting group for an α-amino group at a N-terminus and the washing, and the condensation of the protected amino acids and the washing, are carried out repeatedly, whereby a peptide chain is extended. In the end, a final deprotection reaction is caused, whereby an intended peptide can be synthesized. In the present specification, the "Boc method" refers to a method wherein amino acids in which an α-amino group at an N-terminus is protected by Boc (tert-butoxycarbonyl group) are used, and they are condensed, so as to synthesize a peptide. The peptide synthesis may be conducted with use of an automatic peptide synthesizing device. Examples of the automatic peptide synthesizing device include the A443A type (produced by Applied Biosystems), and PSSM8 (produced by Shimadzu Corporation).

Examples of the protected amino acid include a protected amino acid in which an α-amino group at an N-terminus is protected by a protecting group X; a protected amino acid in which an α-amino group at an N-terminus is protected by a protecting group X and a functional group a of a side chain is protected by a protecting group Y1; a protected amino acid in which an α-amino group at an N-terminus is protected by a protecting group X and a functional group b of a side chain is protected by a protecting group Y2; and a protected amino acid in which an α-amino group at an N-terminus is protected by a protecting group X and a functional group c of a side chain is protected by a protecting group Y3.

The functional group a is a functional group of a side chain of an amino acid to be radioactively labeled. Examples of the functional group a include an amino group or a group having an amino group.

The functional group b is a functional group not to be radioactively labeled, among radioactively-labelable functional groups of side chains of an amino acid. The functional group b is, for example, a functional group of the same type as that of the functional group a, and preferably, a functional group of a side chain of the same amino acid as the amino acid to which the functional group a belongs to.

The functional group c is a functional group of a side chain of an amino acid other than the functional groups a and b.

The protecting group X is a protecting group for an α-amino group at an N-terminus of an amino acid used in the synthesis of a peptide. Examples of the protecting group X include the above-described protecting groups, and the protecting group X may be determined appropriately depending on the peptide synthesizing method. In the case where the peptide synthesizing method is the Fmoc method, the protecting group X is usually Fmoc; in the case where the peptide synthesizing method is the Boc method, the protecting group X is usually Boc.

The protecting groups Y1 to Y3 are protecting groups for functional groups of side chains of amino acids used in the synthesis of a peptide. The protecting group Y1 is a protecting group for the functional group a, the protecting group Y2 is a protecting group for the functional group b, and the protecting group Y3 is a protecting group for the functional group c. Examples of the protecting groups Y1 to Y3 include the above-described protecting groups, and the protecting groups Y1 to Y3 may be determined appropriately depending on the type of the functional group and the peptide synthesizing method. Preferably, the protecting groups Y1 to Y3 different from the protecting group (protecting group X) for the α-amino group at an N-terminus are used.

The protecting group Y2 is preferably different from the protecting group Y1 for the functional group a, in view of that the protecting group Y2 for the functional group b has to be removed selectively upon deprotection, that is, only the protecting group Y2 is removed while the protecting group Y1 for the functional group a is not removed upon deprotection. Further, the protecting group Y2 is more preferably different from both of the protecting groups Y1 and Y3 for the functional groups a and c, in view of that only the protecting group Y2 is removed while the protecting groups Y1 and Y3 for the functional groups a and c are not removed upon deprotection. When the functional groups a and b are amino groups, the protecting group Y2 for the functional group b is a protecting group of a trityl type from the viewpoint of selective deprotection. Furthermore preferably, the protecting group Y2 for the functional group b is a protecting group of a trityl type, and the protecting group Y1 for the functional group a is a protecting group of a carbamate type. Examples of the protecting group of the trityl type include Mmt, Trt, Mtt, and Mtr. From the viewpoint of more selective deprotection, Mmt and Mtt are preferred. Examples of the protecting group of the carbamate type include Fmoc, Boc, Cbz, Alloc, and Troc, among which Boc is preferred particularly.

[Substitution of Protecting Group]

The substitution of a protecting group is to substitute the protecting group for the functional group b, which includes deprotecting the functional group b by removing the protecting group Y2, and thereafter protecting the functional group b by a protecting group Z different from the protecting group Y2.

The deprotection by removal of the protecting group Y2 may be determined appropriately depending on the type of the protecting group Y2. The deprotection by removal of the protecting group Y2 is preferably carried out by deprotecting the functional group b by removing the protecting group Y2, without deprotection of the functional groups a and c, from the viewpoint of selective labeling. The protecting group Z is a protecting group for protecting the functional group b after the functional group b is deprotected by removing the protecting group Y2 therefrom, and it is different from the protecting group Y2. The protecting group Z can be selected appropriately from the above-described protecting groups, and preferably is the same as the protecting group for the α-amino group at the N-terminus (protecting group X) in the synthesis of a peptide. When the peptide synthesis is conducted by the Fmoc method, the protecting group Z is preferably Fmoc.

[Deprotection by Removing Protecting Groups]

The step of deprotection by removing protecting groups includes deprotecting functional groups by removing protecting groups, the functional groups being those other than the functional group b of the side chain of the amino acid that is protected again, so as to obtain a peptide to be radioactively labeled. More specifically, the step includes deprotecting the functional groups a and c by removing the protecting groups Y1 and Y3, respectively. As a result, a peptide to be radioactively labeled is obtained. The peptide has the functional group b protected by the protecting group Z.

The deprotection of the functional groups a and c by removing the protecting groups Y1 and Y3, respectively, is preferably conduced without deprotection of the functional group b. The deprotection of the functional groups a and c by removing the protecting groups Y1 and Y3 may be determined appropriately depending on the types of the protecting groups. The deprotection of the functional groups a and c by removing the protecting groups Y1 and Y3, respectively, may be carried out upon the excision of the peptide from a solid-phase carrier.

The step may include a step of washing and/or isolating and purifying the obtained peptide, which is conducted after deprotection by removing the protecting groups. The isolation and purification can be carried out by a known separating operation for purification of a peptide or a protein. Examples of the separating operation include the ion-exchange chromatography, the hydrophobic chromatography, the reversed phase chromatography, and the high precision liquid chromatography (HPLC), and some of these may be used in combination as required. The purified peptide may be isolated by, for example, concentrating and/or freeze-drying the same, depending on the intended final form.

[Labeling of Peptide]

The labeling is carried out using a peptide in which the functional group b is protected by the protecting group Z and the functional group a is deprotected by removing the protecting group Y1 therefrom. The peptide to be labeled is preferably a peptide in which the functional group b is protected by the protecting group Z and the functional groups a and c are deprotected by removing the protecting groups Y1 and Y3, respectively, from the viewpoint of the selective labeling; and the peptide is more preferably a peptide in which the functional group b is protected by the protecting group Z, the α-amino group at the N-terminus is protected by the protecting group X, and the functional groups a and c are deprotected by removing the protecting groups Y1 and Y3, respectively. This makes it possible to conduct the selective labeling. As a labeling compound, a known compound used in radioactive labeling can be used, and the examples of the same include those described above.

An exemplary peptide to be synthesized is a peptide having two or more amino acids each of which has an amino group on a side chain. Examples of the amino acid having an amino group on a side chain include lysine. Though the length of the peptide to be synthesized is not limited particularly, the length is, for example, 5 or more amino acid residues, preferably 10 to 150 amino acid residues, and more preferably 20 to 80 amino acid residues. The peptide to be synthesized may have, for example, one amino acid having the functional group a on a side chain, or two, three, or more of such amino acids. The peptide to be synthesized is preferably a polypeptide expressed by any one of the following formulae (25) to (28), form the viewpoint that a GLP-1R imaging molecular probe, or more preferably, a molecular probe of the present invention is to be obtained:

|  | (SEQ ID NO. 25) |
|---|---|
| DLSKQMEEFAVRLFIEWLKNGGPSSGAPPPS | (25) |
|  | (SEQ ID NO. 26) |
| LSKQMEEEAVRLFIEWLKNGGPSSGAPPPS | (26) |
|  | (SEQ ID NO. 27) |
| SKQMEEEAVRLFIEWLKNGGPSSGAPPPS | (27) |
|  | (SEQ ID NO. 28) |
| KQMEEEAVRLFIEWLKNGGPSSGAPPPS | (28) |

Further, the labeling method of the present invention, as still another aspect thereof, relates to a method for radioactively labeling a peptide in which a functional group to be labeled is an α-amino group at an N-terminus. The radioactive labeling method of the present aspect can be conducted in the same manner as described above except for the following:

the step of peptide synthesis is conducted using the following:

as the amino acid positioned at the N-terminus, a protected amino acid in which an α-amino group at the N-terminus is protected by a protecting group Y4; a protected amino acid in which an α-amino group at the N-terminus is protected by a protecting group Y4 and a functional group b on a side chain is protected by a protecting group Y2; or a protected amino acid in which an α-amino group at the N-terminus is protected by a protecting group Y4 and a functional group c on a side chain is protected by a protecting group Y3; and as the other amino acid, a protected amino acid selected from the group consisting of a protected amino acid in which an α-amino group at the N-terminus is protected by a protecting group X; a protected amino acid in which an α-amino group at the N-terminus is protected by a protecting group X and a functional group b on a side chain is protected by a protecting group Y2; and a protected amino acid in which an α-amino group at the N-terminus is protected by a protecting group X and a functional group c on a side chain is protected by a protecting group Y3;

the step of deprotection by removing a protecting group includes deprotecting the α-amino group at the N-terminus and the functional group c by removing the protecting groups Y4 and Y3, respectively; and the step of radioactive labeling is conducted by radioactively labeling the α-amino group at the N-terminus with a radioactive labeling compound, and deprotecting the functional group b by removing the protecting group Z.

The protecting group Y4 is a protecting group for the α-amino group of the amino acid positioned at the N-terminus of the peptide, and is preferably different from the protecting groups X and Y2. The step of deprotection by removing the protecting groups preferably include deprotecting the α-amino group at the N-terminus and the functional group c by removing the protecting groups Y4 and Y3, respectively, without deprotection of the functional group b.

[Peptide Producing Method of the Present Invention]

The present invention, as still another aspect thereof, relates to a method for producing a radioactively labeled peptide, wherein the peptide has a plurality of amino acids having radioactively labelable functional groups on side chains, the method including: synthesizing a peptide to be radioactively labeled, using protected amino acids in each of which an α-amino group at an N-terminus and a functional group of a side chain are protected by protecting groups; deprotecting functional groups by removing protecting groups therefrom, the functional groups to be deprotected being functional groups that are not to be radioactively labeled, among the radioactively labelable functional groups of the side chains of the amino acids of the synthesized peptide; protecting, again, the deprotected functional groups of the side chains of the amino acids by protecting groups different from those removed upon the deprotecting; deprotecting, by removing protecting groups, the other functional groups than the functional groups of the side chains of the amino acids that are again protected, so as to obtain a peptide to be radioactively labeled; radioactively labeling the obtained peptide with a labeling compound; and deprotecting the radioactively-labeled peptide by removing protecting groups. The method for producing a radioactively labeled peptide according to the present invention, as another aspect thereof, includes synthesis of a peptide, the deprotection by removing protecting groups, and the radioactive labeling, using the aforementioned labeling method of the present invention.

According to the method for producing a peptide according to the present invention, for example, only an intended functional group can be labeled selectively. Therefore, it is possible to produce a desired peptide that is radioactively labeled, at a high yield. Further, according to the method for producing a peptide according to the present invention, for example, the molecular probe for imaging according to the present invention can be produced efficiently, and preferably, a high-purity molecular probe for imaging according to the present invention can be produced.

In the peptide producing method of the present invention, the functional groups and the protecting groups are the same as those in the labeling method of the present invention, and the peptide synthesis, the deprotection, the radioactive labeling, and the like can be conducted in the same manner as those of the labeling method of the present invention.

The labeling method of the present invention and the peptide producing method of the present invention are explained below, with reference to an exemplary case where the peptide to be labeled was the polypeptide of the formula (25) shown above and the peptide synthesis was carried out by the peptide solid-phase synthesis method. In the peptide, the functional groups a and b are amino groups, the amino acid having, on a side chain, a functional group (functional group a) to be labeled is a lysine at position 4; the amino acid having, on a side chain, a functional group (functional group b) not to be labeled is a lysine at position 19; and an amino acid having the functional group cis asparaginic acid, serine, glycin, glutamine, arginine, asparagine, or tryptophan. The following describes merely one example, and needless to say, the present invention is not limited to this example.

(1) First, the peptide synthesis is carried out using protected amino acids in which the α-amino group at the N-terminus and functional groups on side chains are protected by protecting groups.

The peptide synthesis can be conducted by, for example, the Fmoc method. Specifically, the synthesis can be carried out by fixing a carboxyl group of serine as an amino acid at a C-terminus via a linker to a resin, and binding amino acids one by one from the C-terminus toward the N-terminus.

As the protected amino acids used in the peptide synthesis, a Fmoc-amino acid derivative used in a common Fmoc-peptide synthesis method can be used. Specifically, as an amino acid having a functional group on a side chain (Asp, Ser, Lys, Gln, Glu, Arg, Asn, Trp), an amino acid in which the functional group is protected by a protecting group depending on the type of the functional group and the α-amino group at the N-terminus is protected by Fmoc can be used, and as the other amino acid, an amino acid in which the α-amino group at the N-terminus is protected by Fmoc can be used. As the protecting groups (protecting groups Y1 and Y3) for the functional groups a and c, it is preferable that protecting groups that can be removed for deprotection under the same conditions are selected.

From the viewpoint of selective deprotection, preferably used as the lysine at position 19 that is not to be radioactively labeled is a lysine in which an amino group (functional group b) on a side chain is protected by a protecting group Y2 different from the protecting group Y1 for the amino group (functional group a) on a side chain of the lysine at position 4 to be radioactively labeled. For example, a lysine in which the amino group on the side chain is protected by a carbamate-type protecting group other than Fmoc may be used as the lysine at position 4, and a lysine in which the amino group on the side chain is protected by a trityl-type protecting group may be used as the lysine at position 19.

(2) Next, in the synthesized peptide, the amino group (functional group b) at the side chain of the lysine at position 19 is deprotected by removing the protecting group Y2, and protected by the protecting group Z.

The deprotection is preferably carried out by deprotecting the amino group (functional group b) on the side chain of the lysine at position 19 by removing the protecting group Y2, without deprotecting the amino group (functional group a) on the side chain of the lysine at position 4 and the functional group c, respectively. The deprotection can be carried out appropriately depending on the type of the protecting group Y2 for the functional group b. In the case where the protecting group is a trityl-type protecting group, for example, it can be removed under weak acid conditions. A reagent making the weak acid conditions is, for example, a reagent containing trifluoroacetic acid.

The protecting group Z is a protecting group for the amino group (functional group b) on the side chain of the lysine at position 19 deprotected, and it is different from the protecting group before the deprotection (protecting group Y2). Though the protecting group Z is not limited particularly as long as it is different from the protecting group before the deprotection (protecting group Y2), it is preferably Fmoc as the protecting group (protecting group X) for the α-amino group at the N-terminus. Fmoc can be introduced to the functional group b by, for example, causing a reaction between the functional group b and N-(fluorenylmethyloxycarbonyloxy)succinimide (FmocOSu) under the presence of amine.

(3) Subsequently, the functional groups other than the α-amino group at the N-terminus and the amino group (functional group b) on the side chain of the lysine at position 19 are deprotected, or more specifically, the amino group (functional group a) on the side chain of the lysine at position 4 and the functional group c are deprotected. This causes the following peptide to be obtained: a peptide in which the α-amino group at the N-terminus and the amino group (functional group b) on the side chain of the lysine at position 19 are protected by protecting groups, while the amino group (functional group a) on the side chain of the lysine at position 4 is deprotected. This peptide corresponds to the molecular probe precursor of the present invention described above.

The deprotection can be conducted in accordance with a known method depending on the type of the protecting group removed for deprotection. This deprotection is carried out upon the excision of the peptide from a solid-phase carrier, and for example, the above-described deprotection by removing the protecting group may be carried out under the condition for the excision of the peptide.

(4) The obtained peptide is radioactively labeled with use of a labeling compound.

In the peptide, the amino group (functional group a) on the side chain of the lysine at position 4 to be radioactively labeled is deprotected, and the amino group (functional group b) on the side chain of the lysine at position 19 not to be radioactively labeled is protected by the protecting group Z; and from the viewpoint of reducing the deprotecting operation after the radioactive labeling, preferably, the functional groups c and a are deprotected by removing the protecting groups Y3 and Y1, while the functional group b is protected by the protecting group Z. Using such a peptide, it is possible to selectively radioactively label only the intended site (the amino group on the side chain of the lysine at position 4).

The radioactive labeling can be conducted in accordance with a known method depending on the type of the peptide to be radioactively labeled. Though the labeling compound is not limited particularly, it may be, for example, the labeling compound having a group represented by the chemical formula (I), or a chelate compound bondable to a metal radioactive isotope (metal nuclide). Examples of the metal nuclide include $^{64}$Cu, $^{67}$Ga, $^{68}$Ga, $^{82}$Rb, $^{99m}$Tc, $^{111}$In, and $^{186}$Re. Examples of the chelate compound include diethylenetriaminepentaacetic acid (DTPA), 6-hydrazinoeulysin-3-carboxylic acid (HYNIC), tetraazacyclododecanetetraacetic acid (DOTA), dithiosemicarbazone (DTS), diaminedithiol (DADT), mercaptoacetylglycylglycylglycine (MAG3), monoamidemonoaminedithiol (MAMA), diamidedithiol (DADS), and propylene diamine dioxime (PnAO). From the viewpoint of production of the molecular probe for imaging according to the present invention, the labeling compound is preferably the labeling compound having a group represented by the chemical formula (I), more preferably, the succinimidyl ester compound represented by the chemical formula (III) shown above, and further more preferably, a succinimidyl ester compound represented by the chemical formula (IV) shown above.

(5) Subsequently, the other protecting groups of the thus radioactively labeled peptide are removed for deprotection. As a result, the peptide in which the intended functional group a (amino group on the side chain of the lysine at position 4) is radioactively labeled can be produced.

In this step, the other protecting groups bonding to the peptide, that is, the protecting group of the amino group at the N-terminus, and the amino group (functional group b) on the side chain of the lysine at position 19 not to be radioactively labeled are removed for deprotection. The deprotection can be conducted by a known method depending on the type of the protecting group. In the case where the protecting group is Fmoc, the deprotection can be carried out, for example, under the piperidine conditions. Thus, the molecular probe of the present invention can be produced.

From the viewpoint for the production of a high-purity radioactively-labeled peptide, a purification step may be conducted additionally. The purification step can be carried out, for example, between the step (3) of deprotection and the step (4) of radioactive labeling.

Further, a step of modifying the α-amino group at the N-terminus with a modifying group having no electric charge, or a step of amidating the carboxyl group at the C-terminus may be included additionally.

Hereinafter, the present invention will be described further by way of Examples and Comparative Examples. It should be noted that the present invention is, when interpreted, not limited to the following Examples.

In the description of the present specification, the following abbreviations are used.

OBu: butyl ester group
Boc: butoxycarbonyl group
Trt: trityl group
Pdf    2,2,4,6,7-pentamethyldihydrobenzofuran-5-sulfonyl group
Mmt: 4-methoxytrityl group
Fmoc: 9-fluorenylmethyloxycarbonyl group

EXAMPLES

Binding Assay

Binding assay analysis was conducted using a molecular probe of the formula (29) below (SEQ ID NO. 29) in which an amino group on a side chain of a lysine residue at position 4 was labeled with [$^{127}$I] 3-iodobenzoyl group, and a molecular probe of the formula (30) below (SEQ ID NO. 30) in which an α-amino group at an N-terminus was labeled with [$^{127}$I] 3-iodobenzoyl group.

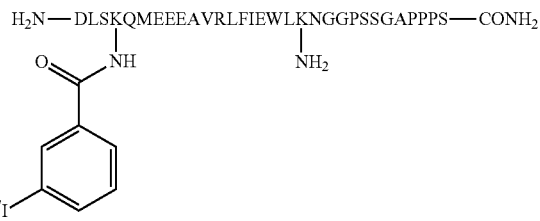

(29)

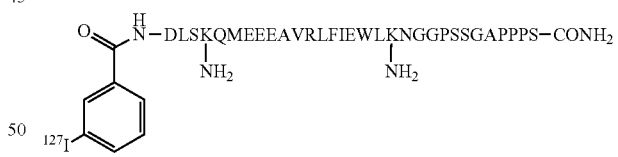

(30)

The above-mentioned molecular probes of the formulae (29) and (30) were prepared by the same method as that for Examples 1 and 2 described below, except that [$^{127}$I]N-succinimidyl 3-iodobenzoate was used in place of [$^{125}$I]N-succinimidyl 3-iodobenzoate.

Pancreatic islets isolated from a mouse was recovered in a 50 ml-tube and after it was subjected to centrifugation (2000 rpm, 2 minutes), it was washed once with 20 mL of cold PBS. To this, 15 mL of trypsin-EDTA (which was prepared by adding 12 mL of PBS-containing 0.53 mM EDTA (pH 7.4 (NaOH)) to 3 mL of trypsine-EDTA (0.05%/0.53 mM) was added. This was incubated at 37° C. for one minute while shaken, then immediately placed on ice. Subsequently, after it was pipetted vigorously 20 times with a 10 mL pipette dropper without being foamed, the cold PBS was added so that the final amount would be 30 mL. After centrifugation (3000 rpm, 2 minutes), it was washed twice with 30 mL of cold PBS. The supernatant was removed, whereby a pancreatic islet cells sample was obtained. The obtained pancreatic islet cells sample was reserved at −80° C.

The pancreatic islet cells sample was suspended in a buffer (20 mM, HEPES (pH 7.4), 1 mM $MgCl_2$, 1 mg/ml bacitracin, 1 mg/ml BSA) so as to make 100 μL/tube. Then, 880 μL of the buffer and 10 μL of a solution including the molecular probe of the above formula (29) or the molecular probe of the above formula (30) (final concentration of molecular probe: 0, $1×10^{-6}$ to $1×10^{-12}$ M), and 10 μL of a solution including [$^{125}$I] Bolton-Hunter-labeled Exendin (9-39) (prepared by adding 90 μL of a buffer to 10 μL of [$^{125}$I]Bolton-Hunter labeled Exendin (9-39) (product code: NEX335, 1.85 MBq/mL=50 μCi/mL, 22.73 pmol/mL=76.57 ng/mL, manufactured by Perkin Elmer) were added thereto, which was incubated for 60 minutes at room temperature. Here, the final concentration of the [$^{125}$I] Bonton-Hunter labeled Exendin (9-39) was set to 0.05 μCi/tube. Next, after B/F separation by aspirating with use of an aspirator to which a moistened glass fiber filter (Whatman GF/C filter) was attached, the filter was washed three times with 5 ml of an ice-cooled PBS. The filter was set in the tube, and the radioactivity measurement was carried out with a gamma counter.

Both of the molecular probe of the above formula (29) in which an amino group on a side chain of a lysine residue at position 4 was labeled with [$^{127}$I] 3-iodobenzoyl group, and the molecular probe of the above formula (30) in which an α-amino group at an N-terminus was labeled with [$^{127}$I] 3-iodobenzoyl group inhibited in a concentration-dependent manner the binding between the GLP-1R and the [$^{125}$I] Boton-Hunter labeled Exendin (9-39). The $IC_{50}$ of the molecular probe of the above formula (29) was $1.6×10^{-9}$ M, and the $IC_{50}$ of the molecular probe of the above formula (30) was $1.4×10^{-9}$M. Thus, both of the molecular probes of the above formulae (29) and (30) exhibited a high affinity with respect to the GLP-1 receptor of pancreatic islets. Moreover, both of the $IC_{50}$ of the molecular probe of the above formula (29) and the $IC_{50}$ of the molecular probe of the above formula (30) were approximate to that of Exendin (9-39) ($IC_{50}$: $1.4× 10^{-9}$M), and thus, with respect to the GLP-1 receptor of pancreatic islets, both of the molecular probes of the above formulae (29) and (30) are considered to have an affinity comparable to that of Exendin (9-39) as a GLP-1 receptor antagonist. Therefore, it was confirmed that both of the molecular probe of the above formula (29) in which an amino group on a side chain of a lysine residue at position 4 was labeled with [$^{127}$I] 3-iodobenzoyl group, and the molecular probe of the above formula (30) in which an α-amino group at an N-terminus was labeled with [$^{127}$I] 3-iodobenzoyl group had sufficient ability of binding to a GLP-1 receptor, particularly to a GLP-1 receptor of pancreatic islets.

Example 1

Using the molecular probe of the formula (31) below (SEQ ID NO. 31), having a configuration in which an amino group of a side chain of a lysine residue at position 4 was labeled with [$^{125}$I] 3-iodobenzoyl group (hereinafter referred to also as "[$^{125}$I]IB label") and a carboxyl group at a C-terminus was amidated in the sequence of SEQ ID NO. 1, biodistribution of the same in a mouse was determined. First, the molecular probe of the formula (31) below was prepared in the following manner.

(31)

$H_2N$—DLSKQMEEEAVRLFIEWLKNGGPSSGAPPPS—$CONH_2$

[structure: 3-iodobenzoyl group with $^{125}I$ attached via NH to side chain, NH_2 shown at another position]

[Preparation of Molecular Probe]

Polypeptide synthesis was performed by using an automatic peptide synthesizer (Model 433A) manufactured by Applied Biosystems, in accordance with the attached software. For the amino acids having functional groups at the side chains, Asp(OBu), Ser(OBu), Lys(Boc), Gln(Trt), Glu(OBu), Arg(Pbf), Asn(Trt) and Trp(Boc) were used respectively. For a lysine at position 19, Lys(Mmt) was used. Rink Amide MBHA (0.125 mmol, 0.34 mmol/g) was employed as the starting resin, the amino acids were extended serially according to the sequence, whereby the polypeptide having the sequence of the following formula (32) was obtained. In the following formula (32), the protecting groups of the side chains other than Lys(Mmt) were not recited.

(SEQ ID NO. 32)
Fmoc-DLSKQMEEEAVRLFIEWLK(Mmt)NGGPSSGAPPPSprotective peptide resin . . . (32)

By a typical process using 1.5% TFA—5% TIS—93.55% $CH_2Cl_2$, the protecting group (Mmt group) of the side chain at a lysine residue at position 19 was removed from the polypeptide of the above formula (32), and the amino group of the side chain at the free lysine residue at position 19 was Fmoc-bonded. Subsequently, removal of all of the protecting groups other than the Fmoc group of the lysine residue at position 19, and excision of peptide from the resin, were carried out by a typical process using 92.5% TFA—2.5% TIS—2.5% $H_2O$—2.5% ethanediol. After completion of the reaction, the carrier resin was removed by filtration, and dry ether was added thereto for precipitating the crude product, which was then filtered. The thus obtained crude product was purified in a linear gradient system of $CH_3CN$—$H_2O$ containing 0.1% TFA, using a liquid chromatograph LC8A manufactured by Shimadzu Corp. (ODS column 3 cm×25 cm). Then, intended fractions were collected by using a fraction collector, and thus the molecular probe precursor of the following formula (33) was obtained as a lyophilized white powder.

(SEQ ID NO. 33)
Fmoc-DLSKQMEEEAVRLFIEWLK(Fmoc)NGGPSSGAPPPS-$NH_2$ (33)

The thus obtained molecular probe precursor (950 μg) of the above-described formula (33) was dissolved in borate buffer (pH 7.8). [$^{125}$I] N-succinimidyl 3-iodobenzoate (SIB) was added thereto so that pH of the reaction solution was adjusted to 8.5 to 9.0. Thus, the precursor was labeled. Thereafter, piperidine was added thereto so as to cause a deprotecting reaction, whereby the intended molecular probe of the above-described formula (31) (molecular probe having a configuration in which the lysine residue at position 4 was labeled in the sequence of SEQ ID NO. 1) was obtained. It should be noted that the α-amino group at the N-terminus is not modified in the molecular probe of the foregoing formula (31).

[Biodistribution]

Figure 1B:
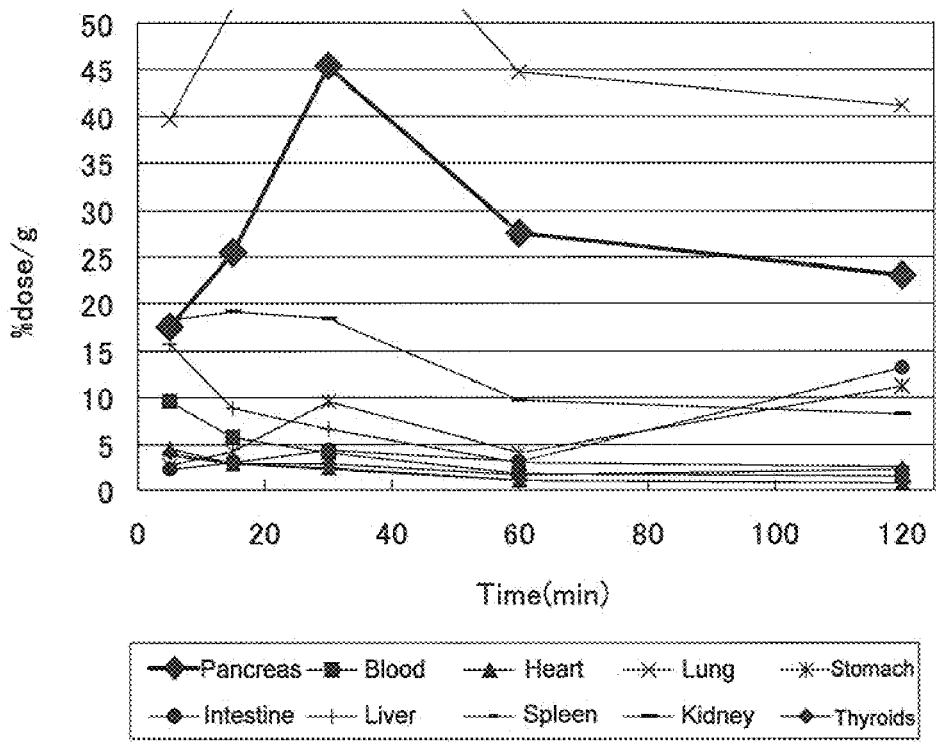

The molecular probe thus prepared (0.57 μCi) of the aforementioned formula (31) was administered to unanesthetized 6-week-old ddY mice (male, weight: 30 g) by intravenous injection (through the tail vein). At points of 5 minutes, 15 minutes, 30 minutes, 60 minutes, and 120 minutes after the administration, organs were dissected out of the mice, respectively (n=5). The weight and the radioactivity of each organ were determined, and an accumulation amount (% dose/g) of the molecular probe was calculated from the radioactivity per unit weight. Exemplary results are shown in Table 1 below, FIGS. 1A and 1B. FIG. 1A is a graph showing how the accumulation of the molecular probe in each organ varied with time, and FIG. 1B is a graph of an enlarged part of FIG. 1A.

TABLE 1

| | Time after administration | | | | |
|---|---|---|---|---|---|
| | 5 min | 15 min | 30 min | 60 min | 120 min |
| Pancreas | 17.53 | 25.43 | 45.37 | 27.49 | 23.02 |
| | (3.43) | (5.09) | (5.87) | (12.49) | (4.74) |
| Blood | 9.62 | 5.73 | 4.03 | 1.84 | 1.54 |
| | (0.99) | (0.43) | (0.57) | (0.46) | (0.42) |
| Heart | 4.55 | 2.91 | 2.46 | 1.03 | 0.74 |
| | (0.29) | (0.42) | (0.19) | (0.16) | (0.08) |
| Lung | 39.67 | 51.64 | 67.29 | 44.74 | 41.21 |
| | (4.48) | (12.04) | (13.73) | (15.20) | (9.63) |
| Stomach | 2.69 | 4.24 | 9.61 | 4.08 | 11.30 |
| | (0.77) | (0.63) | (10.24) | (0.95) | (6.28) |
| Intestine | 2.24 | 2.95 | 4.36 | 3.08 | 13.16 |
| | (0.30) | (0.47) | (2.23) | (0.76) | (16.82) |
| Liver | 15.79 | 8.89 | 6.66 | 3.05 | 2.56 |
| | (0.93) | (0.98) | (0.72) | (0.69) | (0.33) |
| Spleen | 3.73 | 2.86 | 2.28 | 1.11 | 0.71 |
| | (0.62) | (0.48) | (0.54) | (0.33) | (0.16) |
| Kidney | 18.24 | 19.22 | 18.36 | 9.72 | 8.25 |
| | (1.76) | (1.73) | (4.53) | (1.35) | (1.41) |
| Thyroid gland | 4.06 | 2.91 | 2.81 | 1.63 | 2.32 |
| | (0.85) | (0.54) | (0.52) | (0.42) | (0.71) |

Each numerical value indicates an average (SD) of 5 mice.

As shown in Table 1 above, FIGS. 1A and 1B, the accumulation of the molecular probe of the above-described formula (31) into the pancreas was 17.5% dose/g at a point of 5 minutes after the administration, 25.4% dose/g at a point of 15 minutes after the administration, and 45.4% dose/g at a point of 30 minutes after the administration. During a time period from the point of 15 minutes to the point of 120 minutes after the administration, the molecular probe of the foregoing formula (31) accumulated most in the pancreas among the organs other than the lungs, and the accumulation of the molecular probe in the pancreas was maintained at a level exceeding 20% dose/g. During a time period from the point of 15 minutes to the point of 60 minutes after the administration, the accumulation amount of the molecular probe in the pancreas was not less than 4.5 times as much as that in the stomach, not less than 9 times as much as that in the intestine, and not less than 2.5 times as much as that in the liver. Particularly during a time period from the point of 30 minutes to the point of 120 minutes, the accumulation amount of the molecular probe in the pancreas was not less than 6.5 times as much as that in the liver. In other words, it can be concluded that the molecular probe of the formula (31) accumulated specifically in the pancreas. Further, no great change was seen in the accumulation in the thyroid gland, and this suggests that the molecular probe of the formula (31) above was not subjected to deiodization metabolism in vivo. Therefore, the molecular probe of the formula (31) above is considered suitable for the pancreatic β-cell imaging, particularly non-invasive pancreatic β-cell imaging.

Comparative Example

For Comparative Example, using a molecular probe of the following formula (34) (SEQ ID NO. 34), in which an amino group of a side chain of a lysine residue at position 4 was labeled with [$^{125}$I] 3-(3-iodo-4-hydroxyphenyl)propanoyl group (hereinafter referred to also as "[$^{125}$I]BH label") and a carboxyl group at a C-terminus was amidated in the sequence of SEQ ID NO. 1, biodistribution of the same in a mouse was determined. The preparation of the molecular probe of the formula (34) below was carried out in the same manner as that in Example 1, except that the labeling was carried out using the Bolton-Hunter Reagent (produced by Perkin Elmer Inc.). The determination of biodistribution was carried out in the same manner as that in Example 1. Exemplary results of the same are shown in Table 2 below, FIGS. 2A and 2B.

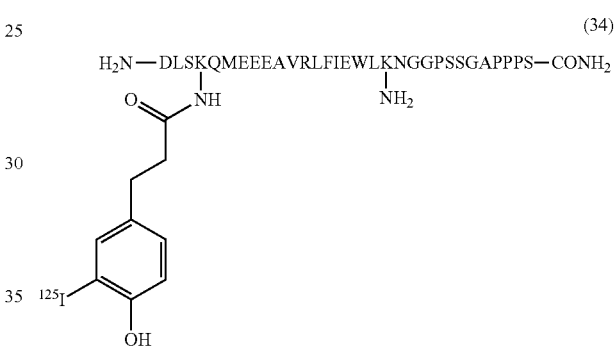

(34)

Incidentally, it is known that in [$^{125}$I] Bolton-Hunter-labeled Extendin (9-39) produced by Perkin Elmer Inc., a lysine residue at position 12 (an amino group of a side chain of a lysine at position 4 in the amino acid sequence of SEQ ID NO. 1) is labeled, like in the molecular probe of the formula (34) above (Suleiman Al-Sabah et al., The positive charge at Lys-288 of the glucagon-like peptide-1 (GLP-1) receptor is important for binding the N-terminus of peptide agonists, FEBS Letters 553 (2003) 342-346).

TABLE 2

| | Time after administration | | | | | |
|---|---|---|---|---|---|---|
| | 2 min | 5 min | 15 min | 30 min | 60 min | 120 min |
| Pancreas | 5.69 | 9.25 | 11.99 | 19.91 | 23.81 | 21.54 |
| | (2.27) | (1.52) | (3.60) | (2.32) | (3.98) | (3.00) |
| Blood | 3.53 | 3.57 | 2.40 | 2.48 | 2.05 | 1.36 |
| | (1.63) | (0.30) | (0.83) | (0.28) | (0.26) | (0.10) |
| Heart | 2.28 | 2.94 | 1.58 | 2.27 | 1.86 | 1.11 |
| | (1.20) | (0.56) | (0.69) | (0.28) | (0.32) | (0.13) |
| Lung | 33.32 | 50.91 | 52.34 | 73.37 | 91.46 | 61.35 |
| | (17.61) | (5.33) | (14.78) | (16.98) | (29.44) | (13.28) |
| Stomach | 1.06 | 1.86 | 1.86 | 2.28 | 3.89 | 9.30 |
| | (0.58) | (0.18) | (0.94) | (0.58) | (0.52) | (3.23) |
| Intestine | 0.82 | 1.11 | 1.13 | 1.85 | 3.42 | 5.50 |
| | (0.36) | (0.10) | (0.44) | (0.45) | (0.63) | (0.54) |
| Liver | 22.13 | 34.45 | 21.01 | 23.22 | 18.02 | 11.09 |
| | (9.19) | (3.78) | (7.09) | (2.80) | (2.69) | (0.53) |
| Spleen | 1.03 | 1.23 | 1.08 | 0.93 | 0.90 | 0.60 |
| | (0.41) | (0.19) | (0.58) | (0.16) | (0.32) | (0.15) |

TABLE 2-continued

| | Time after administration | | | | | |
|---|---|---|---|---|---|---|
| | 2 min | 5 min | 15 min | 30 min | 60 min | 120 min |
| Kidney | 6.01 | 11.43 | 10.69 | 15.99 | 13.95 | 9.57 |
| | (1.89) | (0.60) | (3.25) | (1.88) | (2.57) | (1.05) |
| Thyroid gland | 1.98 | 2.45 | 3.27 | 4.57 | 7.94 | 18.29 |
| | (0.75) | (0.37) | (1.19) | (1.34) | (1.72) | (1.32) |

Each numerical value indicates an average (SD) of 5 mice.

As shown in Tables 1 and 2 above, FIGS. 1A and 1B, and 2A and 2B, the molecular probe of the formula (31) of Example 1 labeled with a [$^{125}$I] 3-iodobenzoyl group was accumulated much in the pancreas in every time period, as compared with the molecular probe of the formula (34) above of Comparative Example labeled with [$^{125}$I]3-(3-iodo-4-hydroxyphenyl)propanoyl group. Particularly, the accumulation amount of the molecular probe of the formula (31) above in the pancreas at a point of 30 minutes after the administration was about twice larger than the accumulation amount of the molecular probe of the formula (34) above of Comparative Example in the pancreas.

Figure 2A:
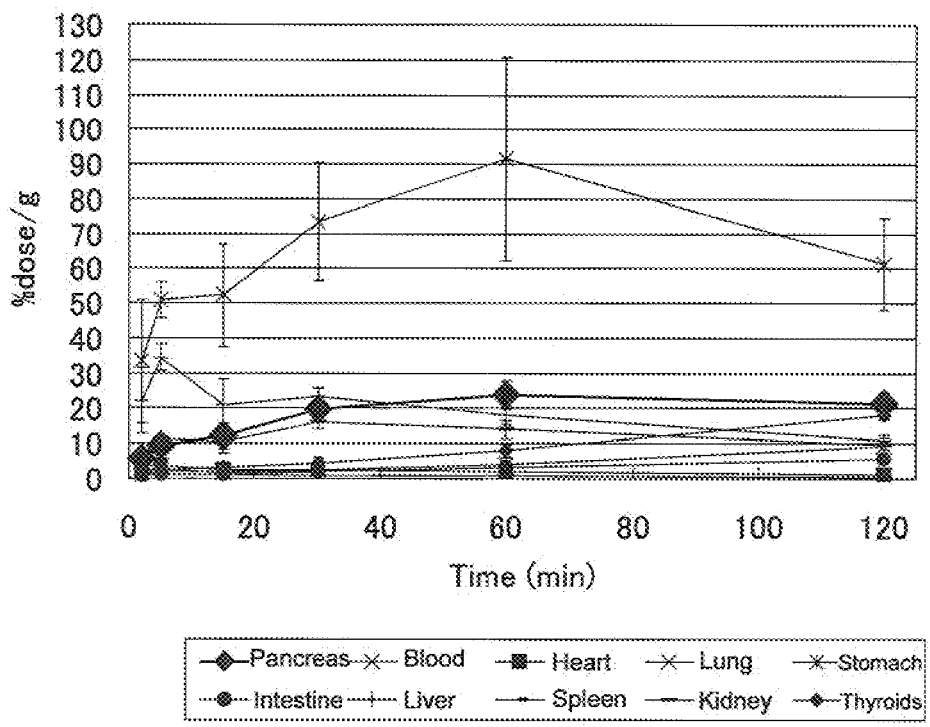
FIGS. 2A and 2B show exemplary graphs showing variations with time of biodistribution of a molecular probe according to Comparative Example.
Figure 2B:
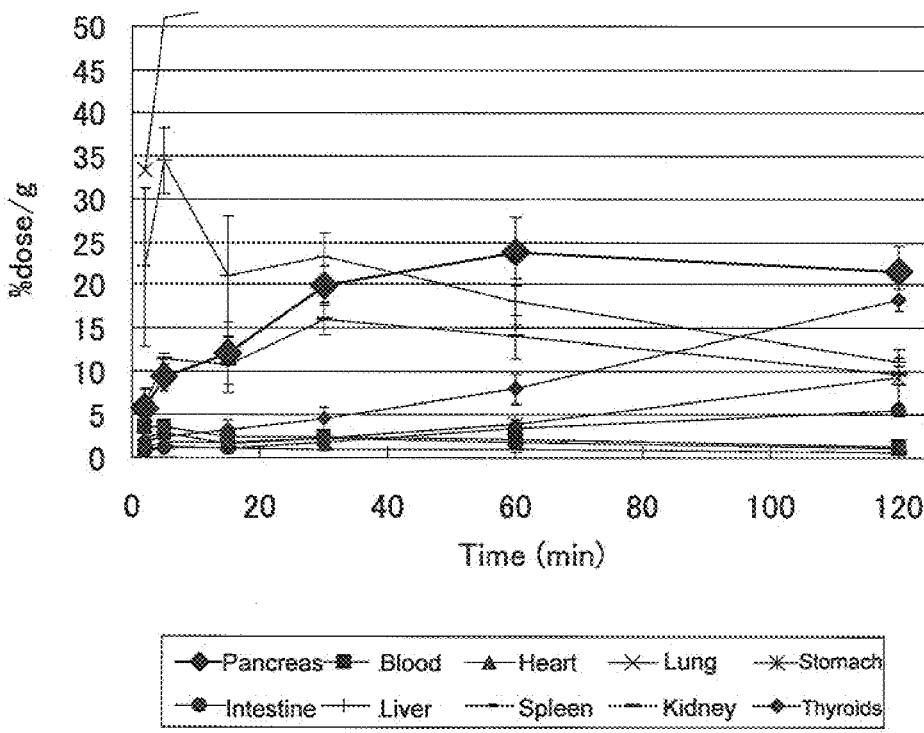

Further, as shown in Table 2 above, FIGS. 2A and 2B, the accumulation of the molecular probe of the formula (34) of Comparative Example in the thyroid gland was increased as time passed, and this suggested that the molecular probe was subjected to deiodization metabolism in vivo. On the other hand, the molecular probe of the formula (31) above did not exhibit increased accumulation in the thyroid gland as shown in Table 1 above, FIGS. 1A and 1B. Thus, it was not subjected to deiodization metabolism in vivo. Therefore, the molecular probe of the formula (31) above labeled with [$^{125}$I] 3-iodobenzoyl group is considered more suitable for the pancreatic β-cell imaging, particularly noninvasive pancreatic β-cell imaging, as compared with the molecular probe of the formula (34) above of Comparative Example labeled with [$^{125}$I] 3-(3-iodo-4-hydroxyphenyl)propanoyl group.

Based on the accumulation amount obtained by the biodistribution experiments on the molecular probe in Example 1 and the molecular probe in Comparative Example, the ratio of pancreas/liver ('accumulation amount in pancreas'/'accumulation amount in liver') for each probe is shown in Table 3 below, and the ratio of pancreas/kidney ('accumulation amount in pancreas'/'accumulation amount in kidney') for each probe is shown in Table 4 below.

TABLE 3

| | Pancreas/Liver Ratio | | | | |
|---|---|---|---|---|---|
| | Time after administration | | | | |
| | 5 min | 15 min | 30 min | 60 min | 120 min |
| Example 1 | 1.11 | 2.91 | 6.84 | 8.73 | 9.05 |
| | (0.21) | (0.71) | (0.78) | (2.21) | (1.83) |
| Com. Example | 0.27 | 0.57 | 0.86 | 1.32 | 1.94 |
| Example 2 | 0.54 | 1.09 | 1.66 | 2.30 | 3.52 |
| | (0.13) | (0.39) | (0.22) | (0.54) | (0.92) |

TABLE 4

| | Pancreas/Kidney Ratio | | | | |
|---|---|---|---|---|---|
| | Time after administration | | | | |
| | 5 min | 15 min | 30 min | 60 min | 120 min |
| Example 1 | 0.97 | 1.34 | 2.54 | 2.75 | 2.79 |
| | (0.21) | (0.29) | (0.42) | (0.90) | (0.30) |
| Com. Example | 0.81 | 1.12 | 1.25 | 1.71 | 2.25 |
| Example 2 | 1.18 | 1.89 | 3.15 | 3.61 | 4.53 |
| | (0.29) | (0.39) | (0.65) | (0.80) | (0.49) |

As shown in the above Tables 3 and 4, the ratio of pancreas/liver and the ratio of pancreas/kidney for the molecular probe of Example 1 (the molecular probe of the above formula (31)) were high compared to the molecular probe of Comparative Example. Particularly, in a time period from the point of 30 minutes to the point of 60 minutes after the administration, the ratio of pancreas/liver of the molecular probe of Example 1 (the molecular probe of the above formula (31)) exceeded 6 times as much as that of the molecular probe of Comparative Example. Thus, it was suggested that clear images of pancreas can be obtained at the time of imaging with the molecular probe of Example 1 where the ratio of accumulation amount in the pancreas to the surrounding organs of the pancreas is high and the accumulation amount in the surrounding organs of the pancreas is low.

[Blocking Experiment]

A blocking experiment was performed by using a molecular probe prepared in Example 1 (the molecular probe of the formula (31)). For the mice, 6-week-old ddY mice (male, weight: about 30 g) were used.

First, non-labeled exendin(9-39) (cold probe, SEQ ID NO. 37) was administered (0.1 mL of 0.5 mg/mL solution) preliminarily by intravenous injection to unanesthetized mice. At a point of 30 minutes after the foregoing preliminary administration, the prepared molecular probe of the formula (31) (5 μCi) was administered by intravenous injection. Then, at a time of 30 minutes after the administration of the molecular probe, the organs were dissected out, respectively (n=5). The weight and the radioactivity of each organ were determined, and an accumulation amount (% dose/g) was calculated from the radioactivity per unit weight. Exemplary results are shown in FIG. 3.

(SEQ ID NO. 37)
H$_2$N-DLSKQMEEEAVRLFIEWLKNGGPSSGAPPPS-NH$_2$   (37)

As a control, without preliminary administration of a cold probe, the prepared molecular probe (5 μCi) of the formula (31) was administered to unanesthetized mice by intravenous injection. Then, at a time of 30 minutes after the administration, the respective organs were dissected (n=5). The weight and the radioactivity of each organ were determined, and an accumulation amount (% dose/g) of the molecular probe was calculated from the radioactivity per unit weight. Exemplary results are shown in FIG. 3, together with the exemplary results for the case including the preliminary administration.

Figure 3:
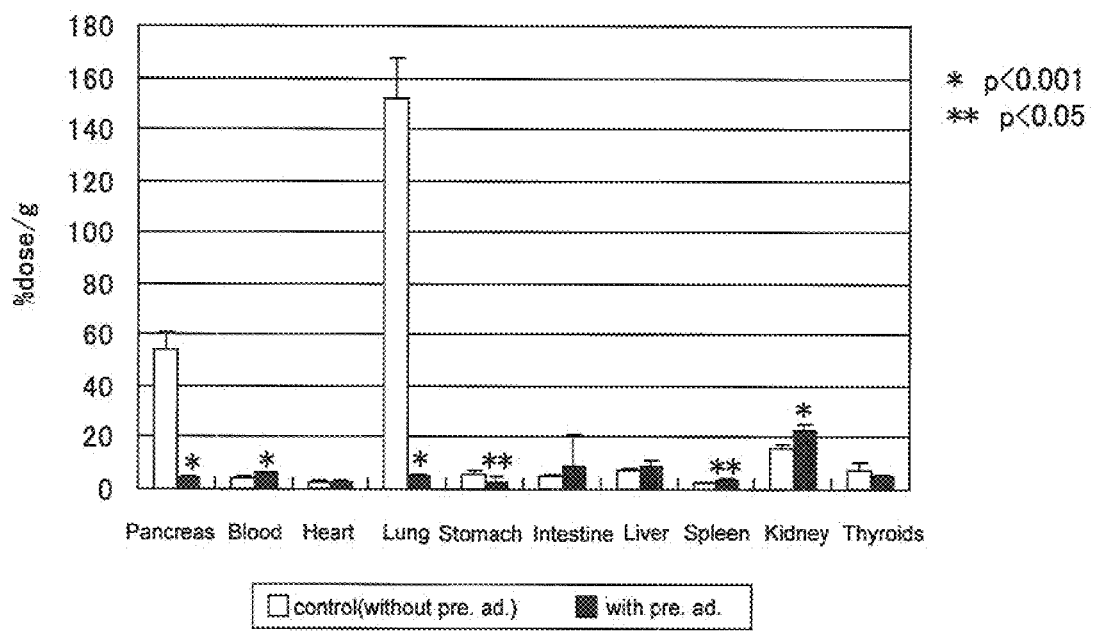
FIG. 3 shows a graph showing exemplary results of a blocking experiment using a molecular probe according to Example 1.

FIG. 3 is a graph showing an accumulation amount (% dose/g) for the case including the preliminary administration and an accumulation amount (% dose/g) for the control (without preliminary administration). As shown in FIG. 3, it was observed that, the binding with a GLP-1 receptor was inhibited by preliminary administration of a cold probe, whereby about 92.2% of the uptake of the molecular probe of the formula (31) was inhibited. Therefore, it can be concluded that the molecular probe of the formula (31) above is bound to the GLP-1 receptor, particularly the GLP-1 receptor of pancreatic islets.

[Two-Dimensional Imaging Analysis]

Two-dimensional imaging analysis was performed using transgenic mice that have a genetic background of $C_{57}BL/6$ mice and express GFP (green fluorescent protein) under regulation of MIP (mouse insulin I gene promoter) (hereinafter these mice are referred to as "MIP-GFP mice"). First, the molecular probe thus prepared of the aforementioned formula (31) (1 μCi) was administered to unanesthetized MIP-GFP mice (male, weight: 20 g) by intravenous injection, and at points of 30 minutes and 60 minutes after the administration, the pancreases were dissected out of the mice, respectively (n=2). Sections were cut out of the dissected pancreases, and each section was placed on a slide glass, covered with a cover glass. Fluorescence and radioactivity (autoradiography) of each section were determined using an image analyzer (trade name: Typhoon 9410, produced by GE Health Care Inc.) (exposure time: 14 hours). Exemplary results of the same are shown in FIG. 4.

Non-labeled exendin(9-39) (cold probe) was administered (0.1 mL of 0.5 mg/mL solution) preliminarily by intravenous injection to unanesthetized MIP-GFP mice (male, weight: 20 g), and these mice were used as controls 1-1. At a point of 30 minutes after the foregoing preliminary administration, the molecular probe of the formula (31) (1 μCi) was administered by intravenous injection. Then, at a time of 30 minutes after the administration of the molecular probe of the formula (31), the pancreases were dissected out of the mice, respectively (n=2). Sections were cut out of the dissected pancreases, and fluorescence and radioactivity of each section were determined in the same manner as described above.

DPP (dipeptidyl peptidase) IV inhibitor (0.1 mL of 6 mg/mL solution) was administered by intravenous injection to unanesthetized MIP-GFP mice (male, weight: 20 g), and these mice were used as controls 1-2. At a point of 30 minutes after the administration of the DPP-IV inhibitor, GLP-1 (0.1 mL of 0.5 mg/mL solution) was administered to these mice, and immediately after this, the molecular probe of the formula (31) (1 μCi) was administered thereto. At a point of 30 minutes after the administration of the molecular probe of the formula (31), the pancreases were dissected out of the mice, respectively (n=2). Sections were cut out of the dissected pancreases, and fluorescence and radioactivity of each section were determined in the same manner as described above. Exemplary results of the controls 1-1 and 1-2 are shown in FIG. 4 together with the results of Example 1.

Figure 4:
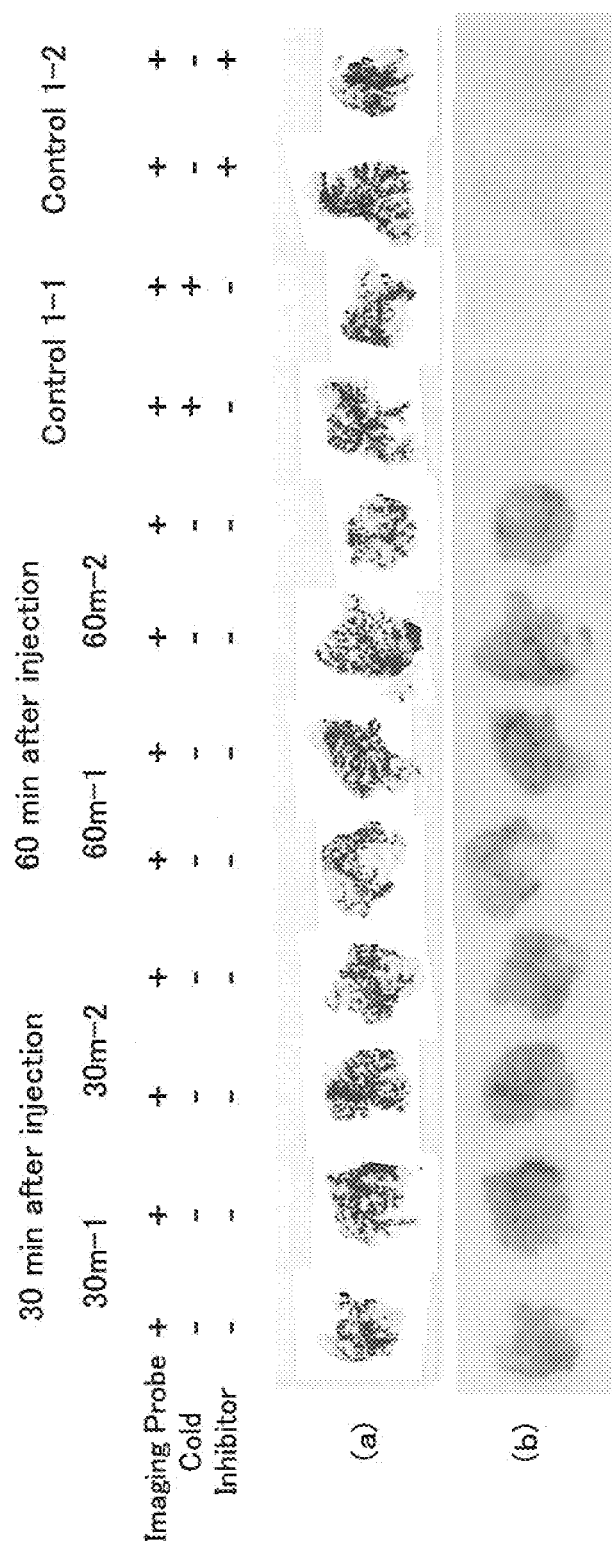
FIG. 4 shows exemplary results of image analysis of a pancreatic islet section using a molecular probe for imaging of pancreatic islets according to Example 1.

FIG. 4 illustrates exemplary results of the imaging analysis of the pancreas sections of the MIP-GFP mice to which the molecular probe of the formula (31) was administered. The images shown therein are images showing a fluorescence signal (a) and a radioactivity signal (b) of each of the sections at the point of 30 minutes after the administration of the molecular probe of the formula (31), the sections at the point of 60 minutes after the administration of the molecular probe of the formula (31), the sections of the controls 1-1, and the sections of the controls 1-2.

As shown in (a) of FIG. 4, a fluorescence GFP signal was observed by an image analyzer in each of the pancreas sections of the MIP-GFP mice. As shown in (b) of FIG. 4, substantially no radioactivity signal was detected from the sections of the controls 1-1 to which the cold probe was administered before the molecular probe of the formula (31) was administered, and the controls 1-2 to which GLP-1 was administered. From this observation, it was found that the binding with a receptor was inhibited by administration of a cold probe or GLP-1, whereby the uptake of the molecular probe of the formula (31) was inhibited. Further, as shown in (a) and (b) of FIG. 4, the localization of the radioactivity signal detected from the labeled molecular probe of the formula (31) was consistent with that of the GFP signal. From this, it was confirmed that the molecular probe of the formula (31) accumulated specifically in the pancreatic β-cells.

Here, all of $^{125}$I, $^{123}$I, and $^{131}$I were γ-ray emitting nuclides. Still further, $^{125}$I and $^{123}$I have the same numbers of nuclear spins. In view of these, it can be presumed that even a molecular probe obtained by replacing the radioactive iodine atom ($^{125}$I) used in the labeling of the molecular probe of the formula (31) with $^{123}$I or $^{131}$I will exhibit behaviors substantially identical to those of the molecular probe of the formula (31). Further, it also can be presumed that even a molecular probe obtained by replacing the radioactive iodine atom ($^{125}$I) with $^{124}$I will exhibit behaviors substantially identical to those of the molecular probe of the formula (31). Thus, it was suggested that using the molecular probe obtained by replacing $^{125}$I of the molecular probe of the formula (31) with $^{123}$I, $^{124}$I, or $^{131}$I, the noninvasive three-dimensional imaging of pancreatic β-cells by SPECT, PET, or the like is enabled, and preferably, the quantification of pancreatic β-cells is enabled.

Example 2

Using the molecular probe of the formula (35) below (SEQ ID NO. 35), having a configuration in which an α-amino group at an N-terminus was labeled with [$^{125}$I] 3-iodobenzoyl group and a carboxyl group at a C-terminus is amidated in the sequence of SEQ ID NO. 5, biodistribution of the same in a mouse was determined. The molecular probe of the formula (35) below was prepared in the same manner in Example 1 except that an amino group labeled was an α-amino group at an N-terminus.

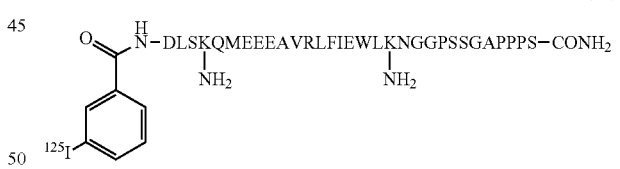

(35)

[Biodistribution]

Figure 5A:
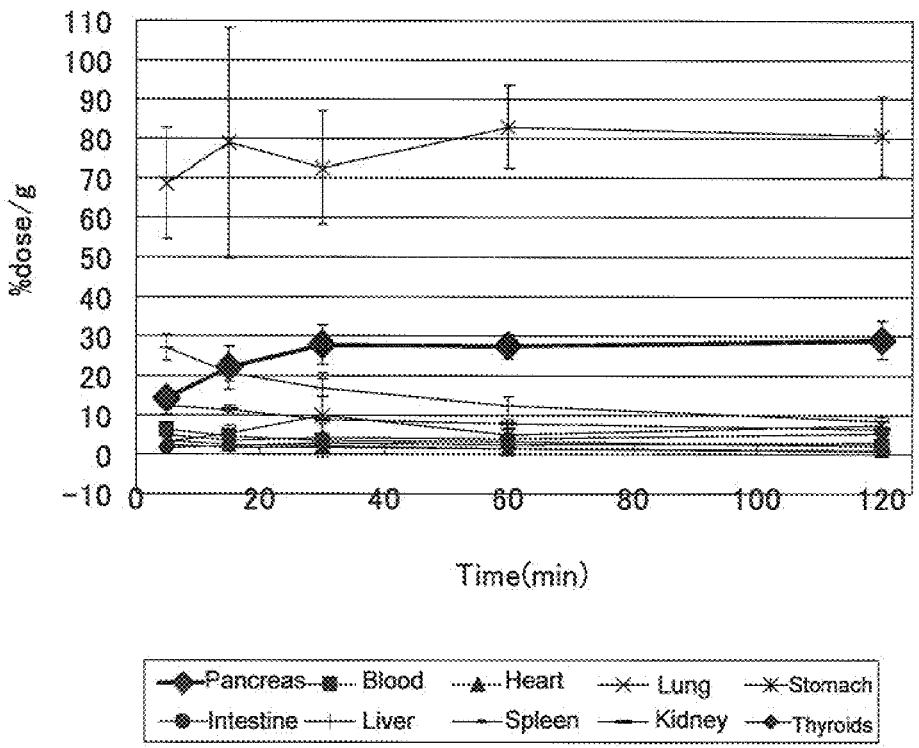
FIGS. 5A and 5B show exemplary graphs showing variations with time of biodistribution of a molecular probe for imaging of pancreatic islets according to Example 2.
Figure 5B:
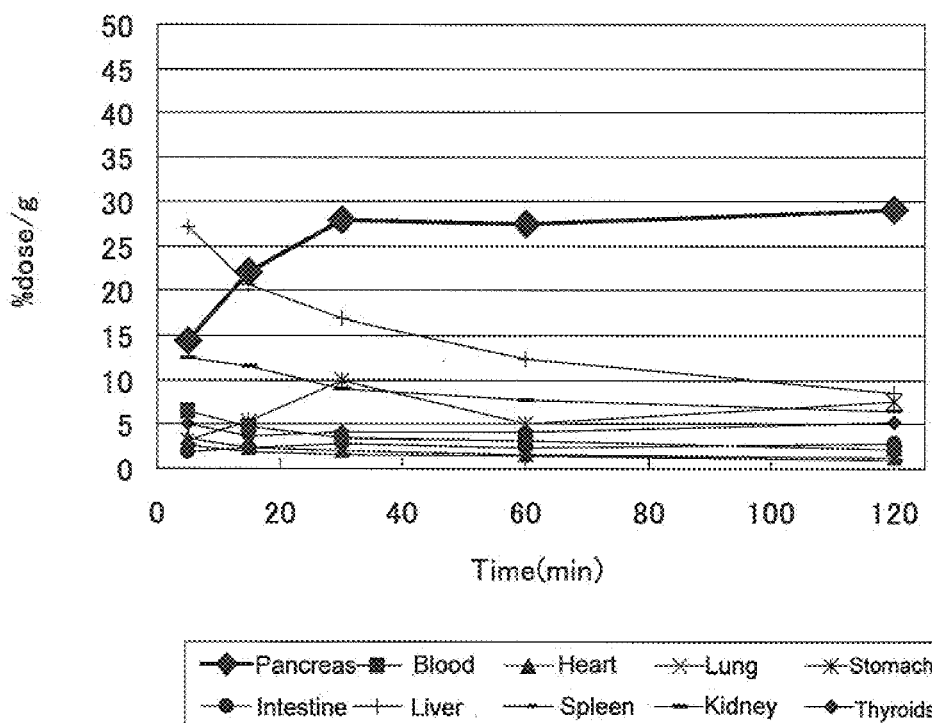

The molecular probe thus prepared of the formula (35) (0.58 μCi) was administered to unanesthetized 6-week-old ddY mice (male, weight: 30 g) by intravenous injection (through the tail vein). At points of 5 minutes, 15 minutes, 30 minutes, 60 minutes, and 120 minutes after the administration, organs were dissected out of the mice, respectively (n=5). The weight and the radioactivity of each organ were determined, and an accumulation amount (% dose/g) of the molecular probe was calculated from the radioactivity per unit weight. Exemplary results are shown in Table 5 below, FIGS. 5A and 5B. FIG. 5A is a graph showing how the accumulation of the molecular probe in each organ varied with time, and FIG. 5B is a graph of an enlarged part of 5A.

TABLE 5

| | Time after administration | | | | |
|---|---|---|---|---|---|
| | 5 min | 15 min | 30 min | 60 min | 120 min |
| Pancreas | 14.34 | 22.01 | 27.92 | 27.47 | 29.04 |
| | (2.49) | (5.49) | (5.10) | (3.04) | (4.81) |
| Blood | 6.53 | 4.80 | 3.45 | 3.10 | 2.24 |
| | (0.38) | (0.22) | (0.49) | (0.59) | (0.29) |
| Heart | 3.55 | 2.40 | 1.99 | 1.54 | 1.20 |
| | (0.60) | (0.48) | (0.17) | (0.44) | (0.19) |
| Lung | 68.73 | 79.05 | 72.66 | 82.90 | 80.59 |
| | (14.19) | (29.24) | (14.51) | (10.50) | (10.19) |
| Stomach | 3.21 | 5.35 | 9.95 | 5.00 | 7.52 |
| | (1.21) | (2.27) | (10.68) | (1.42) | (2.35) |
| Intestine | 1.94 | 2.31 | 2.91 | 2.44 | 2.83 |
| | (0.38) | (0.46) | (0.48) | (0.43) | (0.36) |
| Liver | 27.06 | 20.72 | 16.84 | 12.35 | 8.45 |
| | (3.28) | (2.24) | (2.33) | (2.37) | (1.15) |
| Spleen | 2.67 | 1.92 | 1.62 | 1.37 | 0.88 |
| | (0.77) | (0.20) | (0.29) | (0.36) | (0.23) |
| Kidney | 12.54 | 11.58 | 8.94 | 7.79 | 6.39 |
| | (2.06) | (0.93) | (0.92) | (1.05) | (0.56) |
| Thyroid gland | 5.12 | 3.58 | 4.15 | 4.11 | 5.20 |
| | (0.75) | (0.20) | (0.94) | (1.23) | (0.86) |

Each numerical value indicates an average (SD) of 5 mice.

As shown in above Table 5, FIGS. 5A and 5B, the accumulation of the molecular probe of the above-described formula (35) into the pancreas was 14.3% dose/g at a point of 5 minutes after the administration, 22.0% dose/g at a point of 15 minutes after the administration, 27.9% dose/g at a point of 30 minutes after the administration, 27.5% dose/g at a point of 60 minutes after the administration, and 29% dose/g at a point of 120 minutes after the administration. During a time period from the point of 15 minutes to the point of 120 minutes after the administration, the molecular probe of the foregoing formula (35) was accumulated most in the pancreas among the organs other than the lungs, and the accumulation of the molecular probe in the pancreas was maintained at a level exceeding 20% dose/g. During any time period, the accumulation amount of the molecular probe in the pancreas was not less than 3 times as much as that in the stomach, and not less than 11 times as much as that in the intestine. During a time period from the point of 60 minutes to the point of 120 minutes after the administration, the accumulation amount in the pancreas was not less than 2 times as much as that in the liver. In other words, it can be concluded that the molecular probe of the formula (35) accumulated specifically in the pancreas. Further, no great change was seen in the accumulation in the thyroid gland, and this suggests that the molecular probe of the formula (35) above was not subjected to deiodization metabolism in vivo. Therefore, the molecular probe of the formula (35) above is considered suitable for the pancreatic β-cell imaging, particularly noninvasive pancreatic β-cell imaging.

As shown in the above Tables 3 and 4, the ratio of pancreas/liver and the ratio of pancreas/kidney for the molecular probe of Example 2 (the molecular probe of the above formula (35)) were high in comparison with the molecular probe of Comparative Example. Thus, it was suggested that clear images of pancreas can be obtained at the time of imaging with the molecular probe of Example 2 where the ratio of accumulation amount in the pancreas to the surrounding organs of the pancreas is high and the accumulation amount in the surrounding organs of the pancreas is low.

[Two-Dimensional Imaging Analysis]

The molecular probe thus prepared of the aforementioned formula (35) (0.8 µCi) was administered to unanesthetized MIP-GFP mice (male, weight: 20 g) by intravenous injection, and at points of 30 minutes and 60 minutes after the administration, the pancreases were dissected out of the mice, respectively (n=2). Sections were cut out of the dissected pancreases, and each section was placed on a slide glass, covered with a cover glass Fluorescence and radioactivity of each section (autoradiography) were determined using an image analyzer (trade name: Typhoon 9410, produced by GE Health Care Inc.) (exposure time: 18 hours). Exemplary results of the same are shown in FIG. 6.

Unlabeled exendin(9-39) (cold probe) (0.1 mL of 0.5 mg/mL solution) was preliminarily administered by intravenous injection to unanesthetized MIP-GEP mice (male, weight: 20 g), and these mice were used as controls 2. At a point of 30 minutes after the foregoing preliminary administration, the molecular probe of the formula (35) (0.8 µCi) was administered by intravenous injection. Then, at a time of 30 minutes after the administration of the molecular probe of the formula (35), the pancreases were dissected out of the mice, respectively (n=2). Sections were cut out of the dissected pancreases, and fluorescence and radioactivity of each section thus obtained were determined in the same manner as described above. Exemplary results thereof are shown in FIG. 6, together with the results of Example 2 described above.

Figure 6:
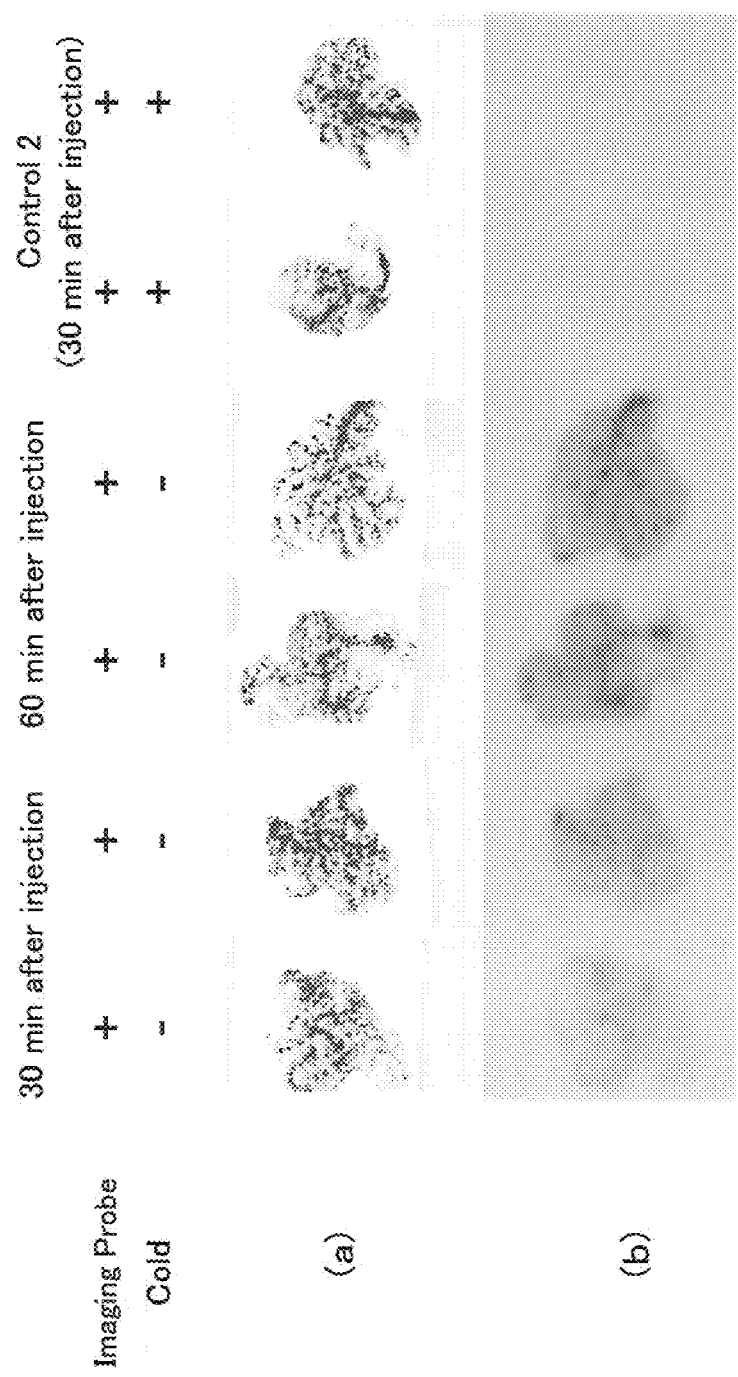
FIG. 6 shows exemplary results of image analysis of a pancreas section using a molecular probe for imaging of pancreatic islets according to Example 2.

FIG. 6 illustrates exemplary results of the imaging analysis of the pancreas sections of the MIP-GFP mice to which the molecular probe of the formula (35) was administered. The images shown therein are images showing a fluorescence signal (a) and a radioactivity signal (b) of each of the sections at the point of 30 minutes after the administration of the molecular probe of the formula (35), the sections at the point of 60 minutes after the administration of the molecular probe of the formula (35), and the sections of the controls 2.

As shown in (a) of FIG. 6, a fluorescence GFP signal was observed by an image analyzer in each of the pancreas sections of the MIP-GFP mice. As shown in (b) of FIG. 6, substantially no radioactivity signal was detected from the sections of the control 2 to which a cold probe was administered before the molecular probe of the formula (35) was administered. From this observation, it was found that the binding with a GLP-1 receptor was inhibited by preliminary administration of a cold probe, whereby the uptake of the molecular probe of the formula (35) was inhibited. Further, as shown in (a) and (b) of FIG. 6, the localization of the radioactivity signal detected from the labeled molecular probe of the formula (35) was consistent with that of the GFP signal. From this, it was confirmed that the molecular probe of the formula (35) accumulated specifically in the pancreatic β-cells.

Here, all of $^{125}$I, $^{123}$I, and $^{131}$I were γ-ray emitting nuclides. Still further, $^{125}$I and $^{123}$I have the same numbers of nuclear spins. In view of these, it can be presumed that even a molecular probe obtained by replacing the radioactive iodine atom ($^{125}$I) used in the labeling of the molecular probe of the formula (35) with $^{123}$I or $^{131}$I will exhibit behaviors substantially identical to those of the molecular probe of the formula (35). Further, it also can be presumed that even a molecular probe obtained by the radioactive iodine atom ($^{125}$I) with $^{124}$I will exhibit behaviors substantially identical to those of the molecular probe of the formula (35). Thus, it was suggested that using the molecular probe obtained by replacing $^{125}$I of the molecular probe of the formula (35) with $^{123}$I, $^{124}$I, or $^{131}$I, for example, the noninvasive three-dimensional imaging of pancreatic β-cells by SPECT, PET, or the like is enabled, and preferably, the quantification of pancreatic β-cells is enabled.

The foregoing results suggest that the molecular probe for imaging according to the present invention enables noninvasive three-dimensional imaging of the pancreas, and particularly, noninvasive three-dimensional imaging of pancreatic β-cells, in humans.

Example 3

Using a molecular probe of the formula (36) below (SEQ ID NO. 36), having a configuration in which an amino group of a side chain of a lysine residue at position 4 was labeled with 3-[$^{123}$I] iodobenzoyl group (hereinafter referred to also as "[$^{123}$I]IB label") and a carboxyl group at a C-terminus is amidated in the sequence of SEQ ID NO. 1, biodistribution of the same in a mouse was determined. The molecular probe of the formula (36) below was prepared in the same manner as in the case of the molecular probe of the aforementioned formula (31) using the molecular probe precursor of the aforementioned formula (31) except that [$^{123}$I] SIB was used in place of [$^{125}$I]SIB.

(36)

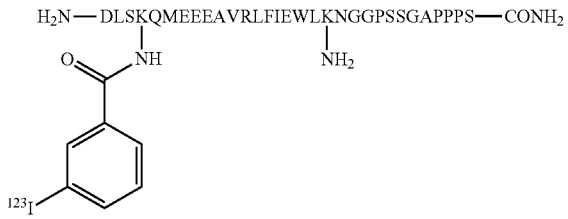

[Three-Dimensional Imaging]

Using the prepared molecular probe of the aforementioned formula (36), SPECT imaging was carried out. The prepared molecular probe of the formula (36) (498 μCi) was administered to anesthetized 5-week-old ddy mice (male, weight: 25 g) by intravenous injection, and the SPECT imaging was carried out. The SPECT imaging was carried out under the following imaging conditions for 21 minutes starting at the point of 30 minutes after the administration, with use of a gamma camera (product name: SPECT 2000H-40, manufactured by Hitachi Medical Corporation). Images obtained were reconfigured under the following reconfiguration conditions.

Imaging Conditions
Collimator: LEPH pinhole collimator
Collecting angle of detector: 360° at 11.25°/40 sec
Collecting time: 40 sec×32 frames, 21 minutes
Reconfiguration Condition
Pretreatment filter: Butterworth filter (order: 10, cutoff frequency: 0.12)

Figure 7:
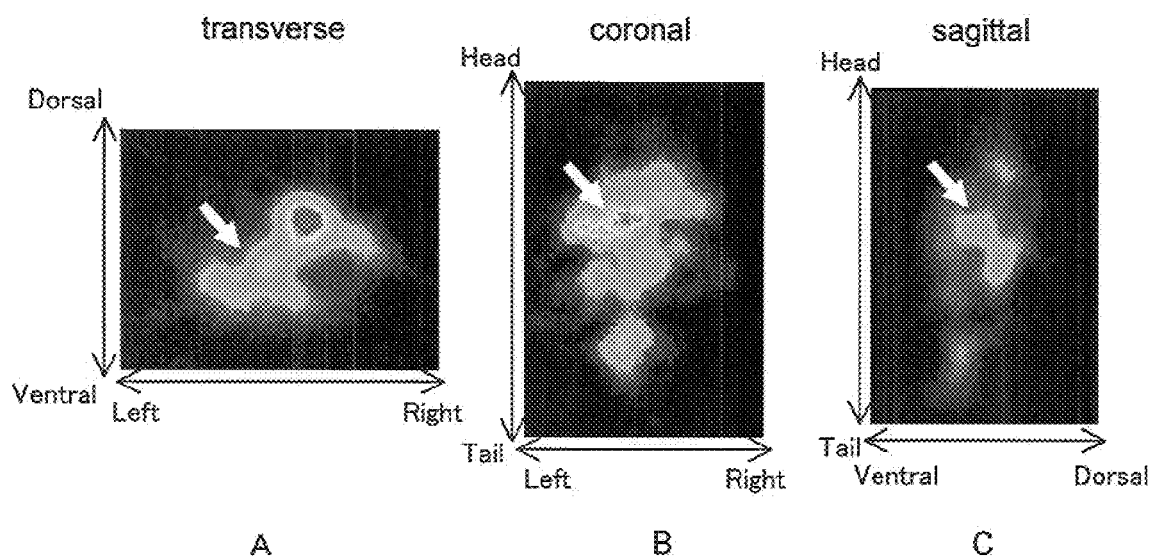
FIGS. 7A to 7C show exemplary SPECT images obtained by using a molecular probe for imaging of pancreatic islets according to Example 3.

Exemplary results are shown in FIGS. 7A to 7C. The images were taken at 30 minutes after the administration of the molecular probe (integrating time: 20 minutes). FIG. 7A shows a transverse view, FIG. '7B shows a coronal view, and FIG. 7C shows a sagittal view. In FIGS. 7A to 7C, the positions of the pancreas are indicated by arrows. It should be noted that the images of FIGS. 7A to 7C are at the same contrast.

As shown in FIGS. 7A to 7C, the position of the pancreas was confirmed noninvasively in mice with use of the molecular probe of the formula (36) above. In other words, it was confirmed that the molecular probe of the present invention enables the noninvasive three-dimensional imaging of the pancreas.

Thus, in view of that the position of the pancreas was confirmed noninvasively in a mouse that has the pancreas in a smaller size than that of a human and in which the organs are present more densely than in a human, this suggests that in a human that has the pancreas in a greater size than that of a mouse and in which the organs are present not as densely as in a mouse, the position of the pancreas and the size of the pancreas can be determined more clearly, and moreover, an amount of expression of the molecular probe in the pancreas can be determined. Therefore, it was suggested that the molecular probe for imaging of the present invention should enable noninvasive three dimensional imaging of the pancreas in a human, particularly noninvasive three-dimensional imaging of pancreatic β-cells.

INDUSTRIAL APPLICABILITY

As described above, the present invention is useful in, for example, the medical field, the molecule imaging field, and the field relating to diabetes.

SEQUENCE LISTING FREE TEXT

SEQ ID NOS. 1 to 12: the amino acid sequences of the molecular probes for imaging of pancreatic islets according to the present invention
SEQ ID NOS. 13 to 24: the amino acid sequences of the molecular probe precursors for imaging of pancreatic islets according to the present invention
SEQ ID NOS. 25 to 28: the amino acid sequences of the peptides used in the labeling method according to the present invention
SEQ ID NOS. 29 to 30: the amino acid sequences of the molecular probes used in the binding assay
SEQ ID NO. 31: the amino acid sequence of the molecular probe for imaging according to Example 1
SEQ ID NO. 32: the amino acid sequence of polypeptide used in the manufacture of the molecular probe for imaging according to Example 1
SEQ ID NO. 33: the amino acid sequence of the molecular probe precursor used in the manufacture of the molecular probe for imaging according to Example 1
SEQ ID NO. 34: the amino acid sequence of the molecular probe of Comparative Example
SEQ ID NO. 35: the amino acid sequence of the molecular probe for imaging according to Example 2
SEQ ID NO. 36: the amino acid sequence of the molecular probe for imaging according to Example 3
SEQ ID NO. 37: the amino acid sequence of Exendin-(9-39)

The invention claimed is:

1. A molecular probe comprising any one of the following polypeptides:
   a polypeptide represented by any one of the following formulae (1) to (4) and (9) to (12) and
   a polypeptide obtained by deletion, insertion, or substitution of one or two amino acids with respect to a polypeptide represented by any one of the following formulae (1) to (12),

Z-DLSXQMEEEAVRLFIEWLKNGGPSSGAPPPS-NH$_2$ (SEQ ID NO. 1) (1)

Z-LSXQMEEEAVRLFIEWLKNGGPSSGAPPPS-NH$_2$ (SEQ ID NO. 2) (2)

Z-SXQMEEEAVRLFIEWLKNGGPSSGAPPPS-NH$_2$ (SEQ ID NO. 3) (3)

Z-XQMEEEAVRLFIEWLKNGGPSSGAPPPS-NH$_2$ (SEQ ID NO. 4) (4)

B-DLSKQMEEEAVRLFIEWLKNGGPSSGAPPPS-NH$_2$ (SEQ ID NO. 9) (9)

B-LSKQMEEEAVRLFIEWLKNGGPSSGAPPPS-NH$_2$ (SEQ ID NO. 10) (10)

B-SKQMEEEAVRLFIEWLKNGGPSSGAPPPS-NH$_2$ (SEQ ID NO. 11) (11)

B-KQMEEEAVRLFIEWLKNGGPSSGAPPPS-NH$_2$ (SEQ ID NO. 12) (12)

where
in the foregoing formulae (1) to (4),
Z- indicates that an α-amino group at an N-terminus is either not modified, or is modified with a modifying group having no electric charge,
X represents a lysine residue, an amino group of a side chain of the lysine residue being labeled with a group represented by the formula (II) below having an aromatic ring,
the polypeptide obtained by deletion, insertion, or substitution of one or two amino acids with respect to a polypeptide represented by any one of the formulae (1) to (4) comprises X,
in the formulae (9) to (12),
B- indicates that an α-amino group at an N-terminus is labeled with a group represented by the formula (II) below having an aromatic ring, and the polypeptide obtained by deletion, insertion, or substitution of one or two amino acids with respect to a polypeptide represented by any one of the formulae (9) to (12) comprises B, and
in the foregoing formulae (1) to (4) and (9) to (12),
—NH$_2$ indicates that a carboxyl group at a C-terminus is amidated,

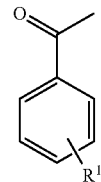

(II)

wherein R$^1$ represents a substituent that contains anyone of $^{123}$I, $^{124}$I, $^{125}$I, and $^{131}$I.

2. A kit for performing imaging of pancreatic islets, comprising the molecular probe according to claim 1.

3. The kit according to claim 2, wherein the molecular probe included in the kit is in a form of a parenteral solution.

4. A reagent for performing imaging of pancreatic islets, comprising the molecular probe according to claim 1.

5. A method for imaging of pancreatic islets comprising detecting a signal of the molecular probe according to claim 1 bound to pancreatic islets preliminarily.

6. The method for imaging of pancreatic islets according to claim 5, further comprising determining a state of pancreatic islets from results of the imaging of pancreatic islets using molecular probe for imaging of pancreatic islets.

7. A method of producing the molecular probe according to claim 1, comprising labeling and deprotecting a precursor of the molecular probe,
   wherein the precursor of the molecular probe includes any one of the following polypeptides:
   a polypeptide represented by any one of the following formulae (13) to (16) and (21) to (24) and
   a polypeptide obtained by deletion, insertion, or substitution of one or two amino acids with respect to a polypeptide represented by any one of the following formulae (13) to (16) and (21) to (24),

```
*-DLSKQMEEEAVRLFIEWLK* NGGPSSGAPPPS-NH₂   (SEQ ID NO. 13)
                                              (13)

*-LSKQMEEEAVRLFIEWLK* NGGPSSGAPPPS-NH₂   (SEQ ID NO. 14)
                                              (14)

*-SKQMEEEAVRLFIEWLK* NGGPSSGAPPPS-NH₂   (SEQ ID NO. 15)
                                              (15)

*-KQMEEEAVRLFIEWLK* NGGPSSGAPPPS-NH₂   (SEQ ID NO. 16)
                                              (16)

DLSK* QMEEEAVRLFIEWLK* NGGPSSGAPPPS-NH₂   (SEQ ID NO. 21)
                                              (21)

LSK* QMEEEAVRLFIEWLK* NGGPSSGAPPPS-NH₂   (SEQ ID NO. 22)
                                              (22)

SK* QMEEEAVRLFIEWLK* NGGPSSGAPPPS-NH₂   (SEQ ID NO. 23)
                                              (23)

K* QMEEEAVRLFIEWLK* NGGPSSGAPPPS-NH₂   (SEQ ID NO. 24)
                                              (24)
``` wherein in the foregoing formulae (13) to (16),

*- indicates that an α-amino group at an N terminus is either protected by a protecting group or modified by a modifying group having no electric charge, and in the foregoing formulae (13) to (16) and (21) to (24), K* indicates that an amino group of a side chain of a lysine is protected by a protecting group, and —NH₂ indicates that a carboxylic group at the C-terminus is amidated, wherein the labeling of the precursor of the molecular probe includes labeling of the precursor with a labeling compound having a group represented by the following formula (II)

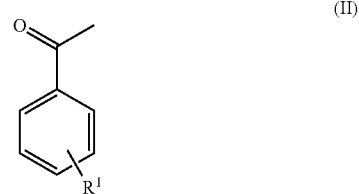

wherein $R^1$ represents a substituent that contains anyone of $^{123}$I, $^{124}$I, $^{125}$I, and $^{131}$I.

8. The molecular probe according to claim 1, wherein the molecular probe comprises the polypeptide represented by any one of the formulae (1) to (4) and (9) to (12).

9. The method according to claim 7, wherein the precursor of the molecular probe for imaging of pancreatic islets includes a polypeptide represented by any one of the formulae (13) to (16) and (21) to (24).

* * * * *

SEQUENCE LISTING

<160> NUMBER OF SEQ ID NOS: 37

<210> SEQ ID NO 1
<211> LENGTH: 31
<212> TYPE: PRT
<213> ORGANISM: Artificial Sequence
<220> FEATURE:

```
<223> OTHER INFORMATION: A molecular probe for imaging of pancreatic
      islets
<220> FEATURE:
<221> NAME/KEY: MOD_RES
<222> LOCATION: (1)..(1)
<223> OTHER INFORMATION: An alpha-amino group of an N-terminus is not
      modified or is modified by a modified group.
<220> FEATURE:
<221> NAME/KEY: MOD_RES
<222> LOCATION: (4)..(4)
<223> OTHER INFORMATION: An amino group of a side chain is labeled.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 1

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: A molecular probe for imaging of pancreatic
      islets
<220> FEATURE:
<221> NAME/KEY: MOD_RES
<222> LOCATION: (1)..(1)
<223> OTHER INFORMATION: An alpha-amino group of an N-terminus is not
      modified or is modified by a modified group.
<220> FEATURE:
<221> NAME/KEY: MOD_RES
<222> LOCATION: (3)..(3)
<223> OTHER INFORMATION: An amino group of a side chain is labeled.
<220> FEATURE:
<221> NAME/KEY: MOD_RES
<222> LOCATION: (30)..(30)
<223> OTHER INFORMATION: A carboxyl group of a C-terminus is amidated.

<400> SEQUENCE: 2

Leu Ser Lys Gln Met Glu Glu Glu Ala Val Arg Leu Phe Ile Glu Trp
1               5                   10                  15

Leu Lys Asn Gly Gly Pro Ser Ser Gly Ala Pro Pro Pro Ser
            20                  25                  30

<210> SEQ ID NO 3
<211> LENGTH: 29
<212> TYPE: PRT
<213> ORGANISM: Artificial Sequence
<220> FEATURE:
<223> OTHER INFORMATION: A molecular probe for imaging of pancreatic
      islets
<220> FEATURE:
<221> NAME/KEY: MOD_RES
<222> LOCATION: (1)..(1)
<223> OTHER INFORMATION: An alpha-amino group of an N-terminus is not
      modified or is modified by a modified group.
<220> FEATURE:
<221> NAME/KEY: MOD_RES
<222> LOCATION: (2)..(2)
<223> OTHER INFORMATION: An amino group of a side chain is labeled.
<220> FEATURE:
<221> NAME/KEY: MOD_RES
<222> LOCATION: (29)..(29)
<223> OTHER INFORMATION: A carboxyl group of a C-terminus is amidated.

<400> SEQUENCE: 3

Ser Lys Gln Met Glu Glu Glu Ala Val Arg Leu Phe Ile Glu Trp Leu
1               5                   10                  15
```

```
Lys Asn Gly Gly Pro Ser Ser Gly Ala Pro Pro Pro Ser
            20                  25

<210> SEQ ID NO 4
<211> LENGTH: 28
<212> TYPE: PRT
<213> ORGANISM: Artificial Sequence
<220> FEATURE:
<223> OTHER INFORMATION: A molecular probe for imaging of pancreatic
      islets
<220> FEATURE:
<221> NAME/KEY: MOD_RES
<222> LOCATION: (1)..(1)
<223> OTHER INFORMATION: An alpha-amino group of an N-terminus is not
      modified or is modified by a modified group. An amino group of a
      side chain is labeled.
<220> FEATURE:
<221> NAME/KEY: MOD_RES
<222> LOCATION: (28)..(28)
<223> OTHER INFORMATION: A carboxyl group of a C-terminus is amidated.

<400> SEQUENCE: 4

Lys Gln Met Glu Glu Glu Ala Val Arg Leu Phe Ile Glu Trp Leu Lys
1               5                   10                  15

Asn Gly Gly Pro Ser Ser Gly Ala Pro Pro Pro Ser
            20                  25

<210> SEQ ID NO 5
<211> LENGTH: 31
<212> TYPE: PRT
<213> ORGANISM: Artificial Sequence
<220> FEATURE:
<223> OTHER INFORMATION: A molecular probe for imaging of pancreatic
      islets
<220> FEATURE:
<221> NAME/KEY: MOD_RES
<222> LOCATION: (1)..(1)
<223> OTHER INFORMATION: An alpha-amino group of an N-terminus is not
      modified or is modified by a modified group.
<220> FEATURE:
<221> NAME/KEY: MOD_RES
<222> LOCATION: (19)..(19)
<223> OTHER INFORMATION: An amino group of a side chain is labeled.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 5

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: A molecular probe for imaging of pancreatic
      islets
<220> FEATURE:
<221> NAME/KEY: MOD_RES
<222> LOCATION: (1)..(1)
<223> OTHER INFORMATION: An alpha-amino group of an N-terminus is not
      modified or is modified by a modified group.
<220> FEATURE:
<221> NAME/KEY: MOD_RES
<222> LOCATION: (18)..(18)
<223> OTHER INFORMATION: An amino group of a side chain is labeled.
<220> FEATURE:
<221> NAME/KEY: MOD_RES
```

```
<222> LOCATION: (30)..(30)
<223> OTHER INFORMATION: A carboxyl group of a C-terminus is amidated.

<400> SEQUENCE: 6

Leu Ser Lys Gln Met Glu Glu Glu Ala Val Arg Leu Phe Ile Glu Trp
1               5                   10                  15

Leu Lys Asn Gly Gly Pro Ser Ser Gly Ala Pro Pro Pro Ser
            20                  25                  30

<210> SEQ ID NO 7
<211> LENGTH: 29
<212> TYPE: PRT
<213> ORGANISM: Artificial Sequence
<220> FEATURE:
<223> OTHER INFORMATION: A molecular probe for imaging of pancreatic
      islets
<220> FEATURE:
<221> NAME/KEY: MOD_RES
<222> LOCATION: (1)..(1)
<223> OTHER INFORMATION: An alpha-amino group of an N-terminus is not
      modified or is modified by a modified group.
<220> FEATURE:
<221> NAME/KEY: MOD_RES
<222> LOCATION: (17)..(17)
<223> OTHER INFORMATION: An amino group of a side chain is labeled.
<220> FEATURE:
<221> NAME/KEY: MOD_RES
<222> LOCATION: (29)..(29)
<223> OTHER INFORMATION: A carboxyl group of a C-terminus is amidated.

<400> SEQUENCE: 7

Ser Lys Gln Met Glu Glu Glu Ala Val Arg Leu Phe Ile Glu Trp Leu
1               5                   10                  15

Lys Asn Gly Gly Pro Ser Ser Gly Ala Pro Pro Pro Ser
            20                  25

<210> SEQ ID NO 8
<211> LENGTH: 28
<212> TYPE: PRT
<213> ORGANISM: Artificial Sequence
<220> FEATURE:
<223> OTHER INFORMATION: A molecular probe for imaging of pancreatic
      islets
<220> FEATURE:
<221> NAME/KEY: MOD_RES
<222> LOCATION: (1)..(1)
<223> OTHER INFORMATION: An alpha-amino group of an N-terminus is not
      modified or is modified by a modified group.
<220> FEATURE:
<221> NAME/KEY: MOD_RES
<222> LOCATION: (16)..(16)
<223> OTHER INFORMATION: An amino group of a side chain is labeled.
<220> FEATURE:
<221> NAME/KEY: MOD_RES
<222> LOCATION: (28)..(28)
<223> OTHER INFORMATION: A carboxyl group of a C-terminus is amidated.

<400> SEQUENCE: 8

Lys Gln Met Glu Glu Glu Ala Val Arg Leu Phe Ile Glu Trp Leu Lys
1               5                   10                  15

Asn Gly Gly Pro Ser Ser Gly Ala Pro Pro Pro Ser
            20                  25

<210> SEQ ID NO 9
<211> LENGTH: 31
<212> TYPE: PRT
<213> ORGANISM: Artificial Sequence
<220> FEATURE:
<223> OTHER INFORMATION: A molecular probe for imaging of pancreatic
      islets
<220> FEATURE:
```

```
<221> NAME/KEY: MOD_RES
<222> LOCATION: (1)..(1)
<223> OTHER INFORMATION: An alpha-amino group of an N-terminus is
      labeled.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 9

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: A molecular probe for imaging of pancreatic
      islets
<220> FEATURE:
<221> NAME/KEY: MOD_RES
<222> LOCATION: (1)..(1)
<223> OTHER INFORMATION: An alpha-amino group of an N-terminus is
      labeled.
<220> FEATURE:
<221> NAME/KEY: MOD_RES
<222> LOCATION: (30)..(30)
<223> OTHER INFORMATION: A carboxyl group of an C-terminus is amidated.

<400> SEQUENCE: 10

Leu Ser Lys Gln Met Glu Glu Glu Ala Val Arg Leu Phe Ile Glu Trp
1               5                   10                  15

Leu Lys Asn Gly Gly Pro Ser Ser Gly Ala Pro Pro Pro Ser
            20                  25                  30

<210> SEQ ID NO 11
<211> LENGTH: 29
<212> TYPE: PRT
<213> ORGANISM: Artificial Sequence
<220> FEATURE:
<223> OTHER INFORMATION: A molecular probe for imaging of pancreatic
      islets
<220> FEATURE:
<221> NAME/KEY: MOD_RES
<222> LOCATION: (1)..(1)
<223> OTHER INFORMATION: An alpha-amino group of an N-terminus is
      labeled.
<220> FEATURE:
<221> NAME/KEY: MOD_RES
<222> LOCATION: (29)..(29)
<223> OTHER INFORMATION: A carboxyl group of a C-terminus is amidated.

<400> SEQUENCE: 11

Ser Lys Gln Met Glu Glu Glu Ala Val Arg Leu Phe Ile Glu Trp Leu
1               5                   10                  15

Lys Asn Gly Gly Pro Ser Ser Gly Ala Pro Pro Pro Ser
            20                  25

<210> SEQ ID NO 12
<211> LENGTH: 28
<212> TYPE: PRT
<213> ORGANISM: Artificial Sequence
<220> FEATURE:
<223> OTHER INFORMATION: A molecular probe for imaging of pancreatic
      islets
<220> FEATURE:
<221> NAME/KEY: MOD_RES
<222> LOCATION: (1)..(1)
```

<223> OTHER INFORMATION: An alpha-amino group of an N-terminus is
      labeled.
<220> FEATURE:
<221> NAME/KEY: MOD_RES
<222> LOCATION: (28)..(28)
<223> OTHER INFORMATION: A carboxyl group of a C-terminus is amidated.

<400> SEQUENCE: 12

Lys Gln Met Glu Glu Glu Ala Val Arg Leu Phe Ile Glu Trp Leu Lys
1               5                   10                  15

Asn Gly Gly Pro Ser Ser Gly Ala Pro Pro Pro Ser
            20                  25

<210> SEQ ID NO 13
<211> LENGTH: 31
<212> TYPE: PRT
<213> ORGANISM: Artificial Sequence
<220> FEATURE:
<223> OTHER INFORMATION: A precursor of a molecular probe for imaging of
      pancreatic islets
<220> FEATURE:
<221> NAME/KEY: MOD_RES
<222> LOCATION: (1)..(1)
<223> OTHER INFORMATION: An alpha-amino group of an N-terminus is
      protected by a protecting group or is modified by a modified
      group.
<220> FEATURE:
<221> NAME/KEY: MOD_RES
<222> LOCATION: (19)..(19)
<223> OTHER INFORMATION: An amino group of a side chain is protected
      by a protecting group.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 13

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: A precursor of a molecular probe for imaging of
      pancreatic islets
<220> FEATURE:
<221> NAME/KEY: MOD_RES
<222> LOCATION: (1)..(1)
<223> OTHER INFORMATION: An alpha-amino group of an N-terminus is
      protected by a protecting group or is modified by a modified
      group.
<220> FEATURE:
<221> NAME/KEY: MOD_RES
<222> LOCATION: (18)..(18)
<223> OTHER INFORMATION: An amino group of a side chain is protected by
      a protecting group.
<220> FEATURE:
<221> NAME/KEY: MOD_RES
<222> LOCATION: (30)..(30)
<223> OTHER INFORMATION: A carboxyl group of a C-terminus is amidated.

<400> SEQUENCE: 14

Leu Ser Lys Gln Met Glu Glu Glu Ala Val Arg Leu Phe Ile Glu Trp
1               5                   10                  15

Leu Lys Asn Gly Gly Pro Ser Ser Gly Ala Pro Pro Pro Ser
            20                  25                  30

```
<210> SEQ ID NO 15
<211> LENGTH: 29
<212> TYPE: PRT
<213> ORGANISM: Artificial Sequence
<220> FEATURE:
<223> OTHER INFORMATION: A precursor of a molecular probe for imaging of
      pancreatic islets
<220> FEATURE:
<221> NAME/KEY: MOD_RES
<222> LOCATION: (1)..(1)
<223> OTHER INFORMATION: An alpha-amino group of an N-terminus is
      protected by a protecting group or is modified by a modified
      group.
<220> FEATURE:
<221> NAME/KEY: MOD_RES
<222> LOCATION: (17)..(17)
<223> OTHER INFORMATION: An amino group of a side chain is protected by
      a protecting group.
<220> FEATURE:
<221> NAME/KEY: MOD_RES
<222> LOCATION: (29)..(29)
<223> OTHER INFORMATION: A carboxyl group of a C-terminus is amidated.

<400> SEQUENCE: 15

Ser Lys Gln Met Glu Glu Glu Ala Val Arg Leu Phe Ile Glu Trp Leu
1               5                   10                  15

Lys Asn Gly Gly Pro Ser Ser Gly Ala Pro Pro Pro Ser
            20                  25

<210> SEQ ID NO 16
<211> LENGTH: 28
<212> TYPE: PRT
<213> ORGANISM: Artificial Sequence
<220> FEATURE:
<223> OTHER INFORMATION: A precursor of a molecular probe for imaging of
      pancreatic islets
<220> FEATURE:
<221> NAME/KEY: MOD_RES
<222> LOCATION: (1)..(1)
<223> OTHER INFORMATION: An alpha-amino group of an N-terminus is
      protected by a protecting group or is modified by a modified
      group.
<220> FEATURE:
<221> NAME/KEY: MOD_RES
<222> LOCATION: (16)..(16)
<223> OTHER INFORMATION: An amino group of a side chain is protected by
      a protecting group.
<220> FEATURE:
<221> NAME/KEY: MOD_RES
<222> LOCATION: (28)..(28)
<223> OTHER INFORMATION: A carboxyl group of a C-terminus is amidated.

<400> SEQUENCE: 16

Lys Gln Met Glu Glu Glu Ala Val Arg Leu Phe Ile Glu Trp Leu Lys
1               5                   10                  15

Asn Gly Gly Pro Ser Ser Gly Ala Pro Pro Pro Ser
            20                  25

<210> SEQ ID NO 17
<211> LENGTH: 31
<212> TYPE: PRT
<213> ORGANISM: Artificial Sequence
<220> FEATURE:
<223> OTHER INFORMATION: A precursor of a molecular probe for imaging of
      pancreatic islets
<220> FEATURE:
<221> NAME/KEY: MOD_RES
<222> LOCATION: (1)..(1)
<223> OTHER INFORMATION: An alpha-amino group of an N-terminus is
      protected by a protecting group or is modified by a modified
      group.
<220> FEATURE:
<221> NAME/KEY: MOD_RES
<222> LOCATION: (4)..(4)
```

```
<223> OTHER INFORMATION: An amino group of a side chain is protected by
      a protecting group.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 17

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: A precursor of a molecular probe for imaging of
      pancreatic islets
<220> FEATURE:
<221> NAME/KEY: MOD_RES
<222> LOCATION: (1)..(1)
<223> OTHER INFORMATION: An alpha-amino group of an N-terminus is
      protected by a protecting group or is modified by a modified
      group.
<220> FEATURE:
<221> NAME/KEY: MOD_RES
<222> LOCATION: (3)..(3)
<223> OTHER INFORMATION: An amino group of a side chain is protected by
      a protecting group.
<220> FEATURE:
<221> NAME/KEY: MOD_RES
<222> LOCATION: (30)..(30)
<223> OTHER INFORMATION: A carboxyl group of a C-terminus is amidated.

<400> SEQUENCE: 18

Leu Ser Lys Gln Met Glu Glu Glu Ala Val Arg Leu Phe Ile Glu Trp
1               5                   10                  15

Leu Lys Asn Gly Gly Pro Ser Ser Gly Ala Pro Pro Pro Ser
            20                  25                  30

<210> SEQ ID NO 19
<211> LENGTH: 29
<212> TYPE: PRT
<213> ORGANISM: Artificial Sequence
<220> FEATURE:
<223> OTHER INFORMATION: A precursor of a molecular probe for imaging of
      pancreatic islets
<220> FEATURE:
<221> NAME/KEY: MOD_RES
<222> LOCATION: (1)..(1)
<223> OTHER INFORMATION: An alpha-amino group of an N-terminus is
      protected by a protecting group or is modified by a modified
      group.
<220> FEATURE:
<221> NAME/KEY: MOD_RES
<222> LOCATION: (2)..(2)
<223> OTHER INFORMATION: An amino group of a side chain is protected by
      a protecting group.
<220> FEATURE:
<221> NAME/KEY: MOD_RES
<222> LOCATION: (29)..(29)
<223> OTHER INFORMATION: A carboxyl group of a C-terminus is amidated.

<400> SEQUENCE: 19

Ser Lys Gln Met Glu Glu Glu Ala Val Arg Leu Phe Ile Glu Trp Leu
1               5                   10                  15

Lys Asn Gly Gly Pro Ser Ser Gly Ala Pro Pro Pro Ser
            20                  25
```

```
<210> SEQ ID NO 20
<211> LENGTH: 28
<212> TYPE: PRT
<213> ORGANISM: Artificial Sequence
<220> FEATURE:
<223> OTHER INFORMATION: A precursor of a molecular probe for imaging of
      pancreatic islets
<220> FEATURE:
<221> NAME/KEY: MOD_RES
<222> LOCATION: (1)..(1)
<223> OTHER INFORMATION: An alpha-amino group of an N-terminus is
      protected by a protecting group or is modified by a modified
      group. An amino group of a side chain is protected by a protecting
      group.
<220> FEATURE:
<221> NAME/KEY: MOD_RES
<222> LOCATION: (28)..(28)
<223> OTHER INFORMATION: A carboxyl group of a C-terminus is amidated.

<400> SEQUENCE: 20

Lys Gln Met Glu Glu Glu Ala Val Arg Leu Phe Ile Glu Trp Leu Lys
1               5                   10                  15

Asn Gly Gly Pro Ser Ser Gly Ala Pro Pro Ser
            20                  25

<210> SEQ ID NO 21
<211> LENGTH: 31
<212> TYPE: PRT
<213> ORGANISM: Artificial Sequence
<220> FEATURE:
<223> OTHER INFORMATION: A precursor of a molecular probe for imaging of
      pancreatic islets
<220> FEATURE:
<221> NAME/KEY: MOD_RES
<222> LOCATION: (4)..(4)
<223> OTHER INFORMATION: An amino group of a side chain is protected by
      a protecting group.
<220> FEATURE:
<221> NAME/KEY: MOD_RES
<222> LOCATION: (19)..(19)
<223> OTHER INFORMATION: An amino group of a side chain is protected by
      a protecting group.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 21

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Ser
            20                  25                  30

<210> SEQ ID NO 22
<211> LENGTH: 30
<212> TYPE: PRT
<213> ORGANISM: Artificial Sequence
<220> FEATURE:
<223> OTHER INFORMATION: A precursor of a molecular probe for imaging of
      pancreatic islets
<220> FEATURE:
<221> NAME/KEY: MOD_RES
<222> LOCATION: (3)..(3)
<223> OTHER INFORMATION: An amino group of a side chain is protected by
      a protecting group.
<220> FEATURE:
<221> NAME/KEY: MOD_RES
<222> LOCATION: (18)..(18)
<223> OTHER INFORMATION: An amino group of a side chain is protected by
      a protecting group.
<220> FEATURE:
<221> NAME/KEY: MOD_RES
<222> LOCATION: (30)..(30)
<223> OTHER INFORMATION: A carboxyl group of a C-terminus is amidated.
```

```
<400> SEQUENCE: 22

Leu Ser Lys Gln Met Glu Glu Glu Ala Val Arg Leu Phe Ile Glu Trp
1               5                   10                  15

Leu Lys Asn Gly Gly Pro Ser Ser Gly Ala Pro Pro Pro Ser
            20                  25                  30

<210> SEQ ID NO 23
<211> LENGTH: 29
<212> TYPE: PRT
<213> ORGANISM: Artificial Sequence
<220> FEATURE:
<223> OTHER INFORMATION: A precursor of a molecular probe for imaging of
      pancreatic islets
<220> FEATURE:
<221> NAME/KEY: MOD_RES
<222> LOCATION: (2)..(2)
<223> OTHER INFORMATION: An amino group of a side chain is protected by
      a protecting group.
<220> FEATURE:
<221> NAME/KEY: MOD_RES
<222> LOCATION: (17)..(17)
<223> OTHER INFORMATION: An amino group of a side chain is protected by
      a protecting group.
<220> FEATURE:
<221> NAME/KEY: MOD_RES
<222> LOCATION: (29)..(29)
<223> OTHER INFORMATION: A carboxyl group of a C-terminus is amidated.

<400> SEQUENCE: 23

Ser Lys Gln Met Glu Glu Glu Ala Val Arg Leu Phe Ile Glu Trp Leu
1               5                   10                  15

Lys Asn Gly Gly Pro Ser Ser Gly Ala Pro Pro Pro Ser
            20                  25

<210> SEQ ID NO 24
<211> LENGTH: 28
<212> TYPE: PRT
<213> ORGANISM: Artificial Sequence
<220> FEATURE:
<223> OTHER INFORMATION: A precursor of a molecular probe for imaging of
      pancreatic islets
<220> FEATURE:
<221> NAME/KEY: MOD_RES
<222> LOCATION: (1)..(1)
<223> OTHER INFORMATION: An amino group of a side chain is protected by
      a protecting group.
<220> FEATURE:
<221> NAME/KEY: MOD_RES
<222> LOCATION: (16)..(16)
<223> OTHER INFORMATION: An amino group of a side chain is protected by
      a protecting group.
<220> FEATURE:
<221> NAME/KEY: MOD_RES
<222> LOCATION: (28)..(28)
<223> OTHER INFORMATION: A carboxyl group of a C-terminus is amidated.

<400> SEQUENCE: 24

Lys Gln Met Glu Glu Glu Ala Val Arg Leu Phe Ile Glu Trp Leu Lys
1               5                   10                  15

Asn Gly Gly Pro Ser Ser Gly Ala Pro Pro Pro Ser
            20                  25

<210> SEQ ID NO 25
<211> LENGTH: 31
<212> TYPE: PRT
<213> ORGANISM: Artificial Sequence
<220> FEATURE:
<223> OTHER INFORMATION: A polypeptide for use in labeling or
      preparation of labelled polypeptide
```

-continued

```
<400> SEQUENCE: 25

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: A polypeptide for use in labeling or
      preparation of labelled polypeptide

<400> SEQUENCE: 26

Leu Ser Lys Gln Met Glu Glu Glu Ala Val Arg Leu Phe Ile Glu Trp
1               5                   10                  15

Leu Lys Asn Gly Gly Pro Ser Ser Gly Ala Pro Pro Pro Ser
            20                  25                  30

<210> SEQ ID NO 27
<211> LENGTH: 29
<212> TYPE: PRT
<213> ORGANISM: Artificial Sequence
<220> FEATURE:
<223> OTHER INFORMATION: A polypeptide for use in labeling or
      preparation of labelled polypeptide

<400> SEQUENCE: 27

Ser Lys Gln Met Glu Glu Glu Ala Val Arg Leu Phe Ile Glu Trp Leu
1               5                   10                  15

Lys Asn Gly Gly Pro Ser Ser Gly Ala Pro Pro Pro Ser
            20                  25

<210> SEQ ID NO 28
<211> LENGTH: 28
<212> TYPE: PRT
<213> ORGANISM: Artificial Sequence
<220> FEATURE:
<223> OTHER INFORMATION: A polypeptide for use in labeling or
      preparation of labelled polypeptide

<400> SEQUENCE: 28

Lys Gln Met Glu Glu Glu Ala Val Arg Leu Phe Ile Glu Trp Leu Lys
1               5                   10                  15

Asn Gly Gly Pro Ser Ser Gly Ala Pro Pro Pro Ser
            20                  25

<210> SEQ ID NO 29
<211> LENGTH: 31
<212> TYPE: PRT
<213> ORGANISM: Artificial Sequence
<220> FEATURE:
<223> OTHER INFORMATION: A molecular probe for use in Binding Assay
<220> FEATURE:
<221> NAME/KEY: MOD_RES
<222> LOCATION: (4)..(4)
<223> OTHER INFORMATION: An amino group of a side chain is labeled by
      [127I]iodobenzoyl.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 29

Asp Leu Ser Lys Gln Met Glu Glu Glu Ala Val Arg Leu Phe Ile Glu
1               5                   10                  15
```

```
Trp Leu Lys Asn Gly Gly Pro Ser Ser Gly Ala Pro Pro Pro Ser
            20                  25                  30

<210> SEQ ID NO 30
<211> LENGTH: 31
<212> TYPE: PRT
<213> ORGANISM: Artificial Sequence
<220> FEATURE:
<223> OTHER INFORMATION: A molecular probe for use in Binding Assay
<220> FEATURE:
<221> NAME/KEY: MOD_RES
<222> LOCATION: (1)..(1)
<223> OTHER INFORMATION: An alpha-amino group of an N-terminus is
      labeled by [127I]3-iodobenzoyl.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 30

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 31
<211> LENGTH: 31
<212> TYPE: PRT
<213> ORGANISM: Artificial Sequence
<220> FEATURE:
<223> OTHER INFORMATION: A molecular probe for imaging of pancreatic
      islets
<220> FEATURE:
<221> NAME/KEY: MOD_RES
<222> LOCATION: (4)..(4)
<223> OTHER INFORMATION: An amino group of a side chain is labeled by
      [125I]3-iodobenzoyl.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 31

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 32
<211> LENGTH: 31
<212> TYPE: PRT
<213> ORGANISM: Artificial Sequence
<220> FEATURE:
<223> OTHER INFORMATION: A polypeptide for preparation of a precursor of
      a molecular probe for imaging of pancreatic islets
<220> FEATURE:
<221> NAME/KEY: MOD_RES
<222> LOCATION: (1)..(1)
<223> OTHER INFORMATION: An alpha-amino group of an N-terminus is
      protected by a Fmoc. A functional group of a side chain is
      protected by a OBu.
<220> FEATURE:
<221> NAME/KEY: MOD_RES
<222> LOCATION: (3)..(3)
<223> OTHER INFORMATION: A functional group of a side chain is protected
      by a OBu.
<220> FEATURE:
<221> NAME/KEY: MOD_RES
<222> LOCATION: (4)..(4)
<223> OTHER INFORMATION: An amino group of a side chain is protected by
      a Boc.
<220> FEATURE:
```

```
<221> NAME/KEY: MOD_RES
<222> LOCATION: (5)..(5)
<223> OTHER INFORMATION: A functional group of a side chain is protected
      by a Trt.
<220> FEATURE:
<221> NAME/KEY: MOD_RES
<222> LOCATION: (7)..(9)
<223> OTHER INFORMATION: A functional group of a side chain is protected
      by a OBu.
<220> FEATURE:
<221> NAME/KEY: MOD_RES
<222> LOCATION: (12)..(12)
<223> OTHER INFORMATION: A functional group of a side chain is protected
      by a Pdf.
<220> FEATURE:
<221> NAME/KEY: MOD_RES
<222> LOCATION: (16)..(16)
<223> OTHER INFORMATION: A functional group of a side chain is protected
      by a OBu.
<220> FEATURE:
<221> NAME/KEY: MOD_RES
<222> LOCATION: (17)..(17)
<223> OTHER INFORMATION: A functional group of a side chain is protected
      by a Boc.
<220> FEATURE:
<221> NAME/KEY: MOD_RES
<222> LOCATION: (19)..(19)
<223> OTHER INFORMATION: An amino group of a side chain is protected by
      a Mmt.
<220> FEATURE:
<221> NAME/KEY: MOD_RES
<222> LOCATION: (20)..(20)
<223> OTHER INFORMATION: A functional group of a side chain is protected
      by a Trt.
<220> FEATURE:
<221> NAME/KEY: MOD_RES
<222> LOCATION: (24)..(25)
<223> OTHER INFORMATION: A functional group of a side chain is protected
      by a OBu.
<220> FEATURE:
<221> NAME/KEY: MOD_RES
<222> LOCATION: (31)..(31)
<223> OTHER INFORMATION: A functional group of a side chain is protected
      by a OBu.

<400> SEQUENCE: 32

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 33
<211> LENGTH: 31
<212> TYPE: PRT
<213> ORGANISM: Artificial Sequence
<220> FEATURE:
<223> OTHER INFORMATION: A precursor of a molecular probe for imaging of
      pancreatic islets
<220> FEATURE:
<221> NAME/KEY: MOD_RES
<222> LOCATION: (1)..(1)
<223> OTHER INFORMATION: An amino group of an N-terminus is protected by
      a Fmoc.
<220> FEATURE:
<221> NAME/KEY: MOD_RES
<222> LOCATION: (19)..(19)
<223> OTHER INFORMATION: An amino group of a side chain is protected by
      a Fmoc.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 33

Asp Leu Ser Lys Gln Met Glu Glu Glu Ala Val Arg Leu Phe Ile Glu
1               5                   10                  15
```

-continued

```
Trp Leu Lys Asn Gly Gly Pro Ser Ser Gly Ala Pro Pro Pro Ser
            20                  25                  30

<210> SEQ ID NO 34
<211> LENGTH: 31
<212> TYPE: PRT
<213> ORGANISM: Artificial Sequence
<220> FEATURE:
<223> OTHER INFORMATION: A molecular probe of comparative example
<220> FEATURE:
<221> NAME/KEY: MOD_RES
<222> LOCATION: (4)..(4)
<223> OTHER INFORMATION: An amino group of a side chain is labeled by
      [125I]3-(3-iodo-4-hydroxyphenyl)propanoyl.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 34

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 35
<211> LENGTH: 31
<212> TYPE: PRT
<213> ORGANISM: Artificial Sequence
<220> FEATURE:
<223> OTHER INFORMATION: A molecular probe for imaging of pancreatic
      islets
<220> FEATURE:
<221> NAME/KEY: MOD_RES
<222> LOCATION: (1)..(1)
<223> OTHER INFORMATION: An alpha-amino group of an N-terminus is
      labeled by [125I]3-iodobenzoyl.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 35

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 36
<211> LENGTH: 31
<212> TYPE: PRT
<213> ORGANISM: Artificial Sequence
<220> FEATURE:
<223> OTHER INFORMATION: A molecular probe for imaging of pancreatic
      islets
<220> FEATURE:
<221> NAME/KEY: MOD_RES
<222> LOCATION: (4)..(4)
<223> OTHER INFORMATION: An amino group of a side chain is labeled by
      [123I]3-iodobenzoyl.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 36

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30
```

```
<210> SEQ ID NO 37
<211> LENGTH: 31
<212> TYPE: PRT
<213> ORGANISM: Artificial Sequence
<220> FEATURE:
<223> OTHER INFORMATION: Exendin-(9-39)
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 37

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30
```